US009070016B2

(12) United States Patent
Su et al.

(10) Patent No.: US 9,070,016 B2
(45) Date of Patent: *Jun. 30, 2015

(54) BIOMETRIC AUTHENTICATION APPARATUS, BIOMETRIC AUTHENTICATION METHOD AND RECORDING MEDIUM

(71) Applicant: NEC CORPORATION, Tokyo (JP)

(72) Inventors: Leiming Su, Tokyo (JP); Yukio Hoshino, Kanagawa (JP); Yukio Itakura, Kanagawa (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,250

(22) Filed: Oct. 11, 2013

(65) Prior Publication Data

US 2014/0037153 A1   Feb. 6, 2014

Related U.S. Application Data

(63) Continuation of application No. 13/144,825, filed as application No. PCT/JP2010/050735 on Jan. 21, 2010, now Pat. No. 8,588,479.

(30) Foreign Application Priority Data

Jan. 22, 2009 (JP) ................................ 2009-012377

(51) Int. Cl.
G06K 9/00 (2006.01)
A61B 5/117 (2006.01)
G07C 9/00 (2006.01)

(52) U.S. Cl.
CPC .............. *G06K 9/0061* (2013.01); *A61B 5/117* (2013.01); *G06K 9/00617* (2013.01); *G07C 9/00158* (2013.01)

(58) Field of Classification Search
CPC ....................... G06K 9/00597; G06K 9/00885
USPC ........................................................ 382/117
See application file for complete search history.

(56) References Cited

U.S. PATENT DOCUMENTS 5,291,560 A * 3/1994 Daugman ..................... 382/117
6,217,172 B1 * 4/2001 Shibutani et al. ............. 351/204
(Continued)

FOREIGN PATENT DOCUMENTS

JP   H08-504979 A   5/1996
JP   2006-146343 A   6/2006
WO   94/09446 A     4/1994

OTHER PUBLICATIONS

"Hironobu Takano, Hiroki Kobayashi, and Kiyomi Nakamura", "Iris Recognition Independent of Rotation and Ambient Lighting Variations", "2006 International Joint Conference on Neural Networks, Vancouver, BC, Canada", Jul. 16-21, 2006.*

(Continued)

*Primary Examiner* — Stephen R Koziol
*Assistant Examiner* — Shaghayegh Azima
(74) *Attorney, Agent, or Firm* — Sughrue Mion, PLLC

(57) ABSTRACT

A plurality of pieces of information related to the iris pattern of an eye can be checked against each other in a short time. Characteristic curves (S(1)-S(8)), which are in accordance with eight ring areas (A1-A8) formed by dividing an image of an iris, are generated. The polarities of the gradients of these characteristic curves are then arranged, thereby generating codes (1-8) to be checked. Each of these codes (1-8) to be checked consists of a ternary combination of +, − and zero, whereby the amount of data to be handled during the checking process can be reduced. As a result, checking the codes to be checked can be performed in a short time.

5 Claims, 26 Drawing Sheets

(56) References Cited

U.S. PATENT DOCUMENTS

| | | | |
|---|---|---|---|
| 6,247,813 B1* | 6/2001 | Kim et al. | 351/206 |
| 6,546,121 B1* | 4/2003 | Oda | 382/117 |
| 7,436,986 B2* | 10/2008 | Caldwell | 382/117 |
| 7,486,806 B2* | 2/2009 | Azuma et al. | 382/117 |
| 7,715,594 B2* | 5/2010 | Ko et al. | 382/117 |
| 8,254,642 B2* | 8/2012 | Kobayashi et al. | 382/117 |
| 2005/0008200 A1* | 1/2005 | Azuma et al. | 382/117 |
| 2006/0120570 A1* | 6/2006 | Azuma et al. | 382/117 |
| 2006/0291702 A1* | 12/2006 | Miessbacher | 382/117 |
| 2007/0014438 A1* | 1/2007 | Ko et al. | 382/117 |
| 2007/0071287 A1* | 3/2007 | Sugita et al. | 382/117 |
| 2007/0201728 A1* | 8/2007 | Monro | 382/117 |
| 2009/0169064 A1* | 7/2009 | Kim et al. | 382/117 |
| 2010/0020107 A1* | 1/2010 | Chui | 345/690 |
| 2010/0246903 A1* | 9/2010 | Cottard | 382/117 |

OTHER PUBLICATIONS

Japanese Office Action for JP Application No. 2012-241127 mailed on Dec. 3, 2013 with English Translation.

* cited by examiner

FIG. 20A

| POLAR COORDINATE | $\theta_1$ | $\theta_2$ | $\theta_3$ | $\theta_4$ | $\theta_5$ | $\theta_6$ | $\theta_7$ | $\theta_8$ | ... | $\theta_{256}$ |
|---|---|---|---|---|---|---|---|---|---|---|
| POLARITY | + | + | + | + | + | 0 | 0 | − | ... | + |

FIG. 20B

| CODE | M1(1) | M1(2) | M1(3) | M1(4) | M1(5) | M1(6) | M1(7) | M1(8) | ... | M1(256) |
|---|---|---|---|---|---|---|---|---|---|---|
| POLARITY | + | + | + | + | + | 0 | 0 | − | ... | + |

BIOMETRIC AUTHENTICATION APPARATUS, BIOMETRIC AUTHENTICATION METHOD AND RECORDING MEDIUM

The present application is a Continuation application of Ser. No. 13/144,825 filed on Jul. 15, 2011, which is a National Stage Entry of International Application PCT/JP2010/050735, filed on Jan. 21, 2010, which claims the benefit of priority from Japanese Patent Application 2009-012377 filed on Jan. 22, 2009, the disclosures of all of which are incorporated in their entirety by reference herein.

TECHNICAL FIELD

The present invention relates to a biometric authentication apparatus, a biometric authentication method and recording medium, and more particularly relates to a biometric authentication apparatus for accomplishing authentication using the iris pattern of an eye, a biometric authentication method for accomplishing authentication using the iris pattern of an eye, and a recording medium readable by a computer.

BACKGROUND ART

In recent years, research and development has flourished on biometric authentication technology that uses physical characteristics of an individual in place of codes and passwords made by combining characters and numbers. In biometric authentication, physical characteristics that differ between individuals are typically used, such as fingerprints, the vein pattern on the back of the hand, the iris pattern of an eye, the voiceprint or the like. In particular, biometric authentication using fingerprints or the vein pattern on the back of the hand have begun to be installed in various systems such as ATMs (Automatic Teller Machines) and personal computers (PCs) as authentication precision has increased and device costs have come down.

However, authentication using fingerprints or the vein pattern on the back of the hand requires the target individual to make part of the body such as the fingers or the hand come into contact with or become close to a certain degree to the apparatus. Consequently, biometric authentication technology using the iris pattern of an eye has attracted attention recently. (For example, see Patent Literature 1).

PRIOR ART LITERATURE

Patent Literature

Patent Literature 1: Japanese Patent Publication No. 3307936

DISCLOSURE OF INVENTION

Problems Overcome by the Invention

With an authentication system that uses iris pattern, there is a tradeoff in the relationship between comparison accuracy and comparison speed. In addition, with an authentication system, the comparison accuracy for properties should be maintained at a defined level or higher. For that reason, improving processing speed while maintaining comparison accuracy in the authentication system is one issue that has been difficult to realize.

In consideration of the foregoing, it is an object of the present invention to provide a biometric authentication apparatus, a biometric authentication method and a recording medium that can accomplish in a short time comparison of information related to the iris pattern of an eye.

Problem Resolution Means

The biometric authentication apparatus according to a first aspect of the present invention comprises a curve calculating unit for calculating, based on a digital image of an iris, curves showing the relationship between polar coordinates indicating the position of the iris on the digital image and the luminance of pixels comprising the digital image of the iris corresponding to the coordinate values of the polar coordinates; and a code generating unit for generating a comparison target code by arranging the polarities of the slopes of the curve in order of the polar coordinate.

The biometric authentication method according to a second aspect of the present invention has a process for calculating, based on the digital image of the iris, curves showing the relationship between polar coordinates indicating the position of the iris on the digital image and the luminance of pixels comprising the digital image of the iris corresponding to the coordinate values of the polar coordinates; and a process for generating a comparison target code by arranging the polarities of the slopes of the curves in order of the polar coordinate.

The recording medium according to a third aspect of the present invention stores a program that causes a computer to functions as a means for calculating, based on the digital image of the iris, curves showing the relationship between polar coordinates indicating the position of the iris on the digital image and the luminance of pixels comprising the digital image of the iris corresponding to the coordinate values of the polar coordinates; and a means for generating a comparison target code by arranging the polarities of the slopes of the curves in order of the polar coordinate.

Efficacy of the Invention

With the present invention, it is possible to accomplish in a short time comparison of information related to the iris pattern of an eye.

BRIEF DESCRIPTION OF DRAWINGS

FIG. 20A is a drawing (part 1) for explaining the method of generating comparison target codes.

FIG. 20B is a drawing (part 2) for explaining the method of generating comparison target codes.

BEST MODE FOR CARRYING OUT THE INVENTION (First Embodiment)

Figure 1:
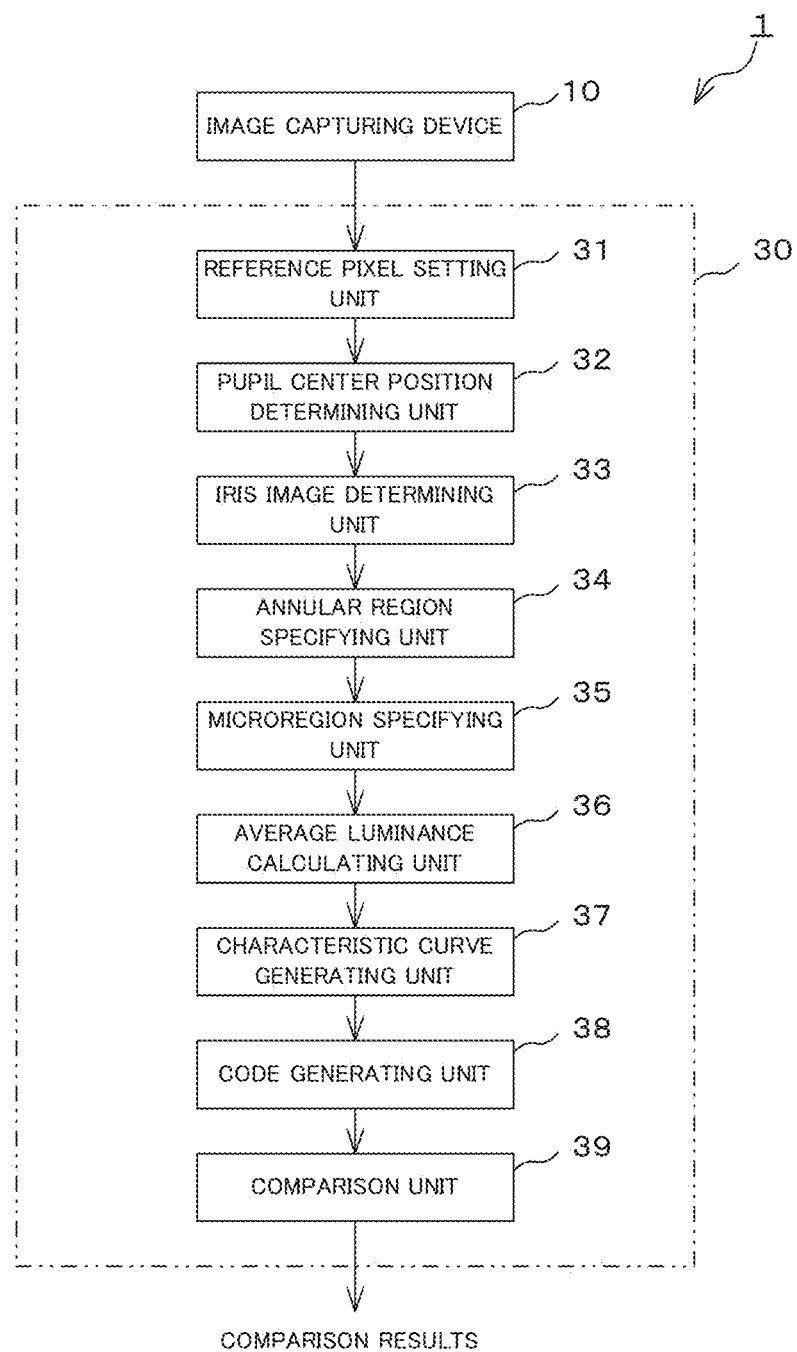
FIG. 1 is a block diagram of a biometric authentication apparatus according to a first embodiment of the present invention.

A first embodiment of the present invention is described below with reference to FIGS. 1 to 20. FIG. 1 is a block diagram showing the summary composition of a biometric authentication apparatus 1 according to this embodiment. The biometric authentication apparatus 1 is an apparatus that accomplishes authentication using the iris pattern of the target individual. The biometric authentication apparatus 1 includes an image capturing device 10 and a comparison apparatus 30.

Figure 2:
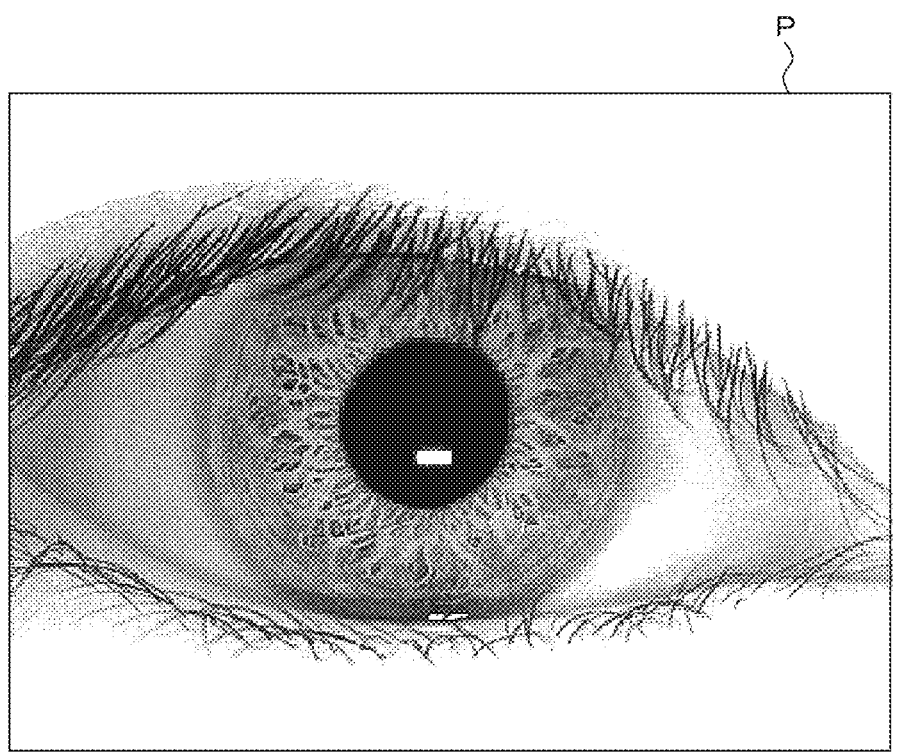
FIG. 2 shows a digital image.

The image capturing device 10 includes, for example, an illumination apparatus for shining illuminating light including near-infrared rays, and an infrared ray camera having an infrared ray filter for cutting visible light other than infrared rays. Furthermore, the image capturing device 10 outputs to the comparison apparatus 30 a digital image obtained by photographing an eye of the target individual. FIG. 2 shows a digital image P that is one example of a digital image captured by the image capturing device 10. As can be seen from FIG. 2, with the image capturing device 10 at least an iris of the target individual and a portion of the eyelid and eyelashes surrounding that are captured. In addition, with the image capturing device 10, an image is captured using infrared light, so the digital image P is a grayscale image.

Figure 3:
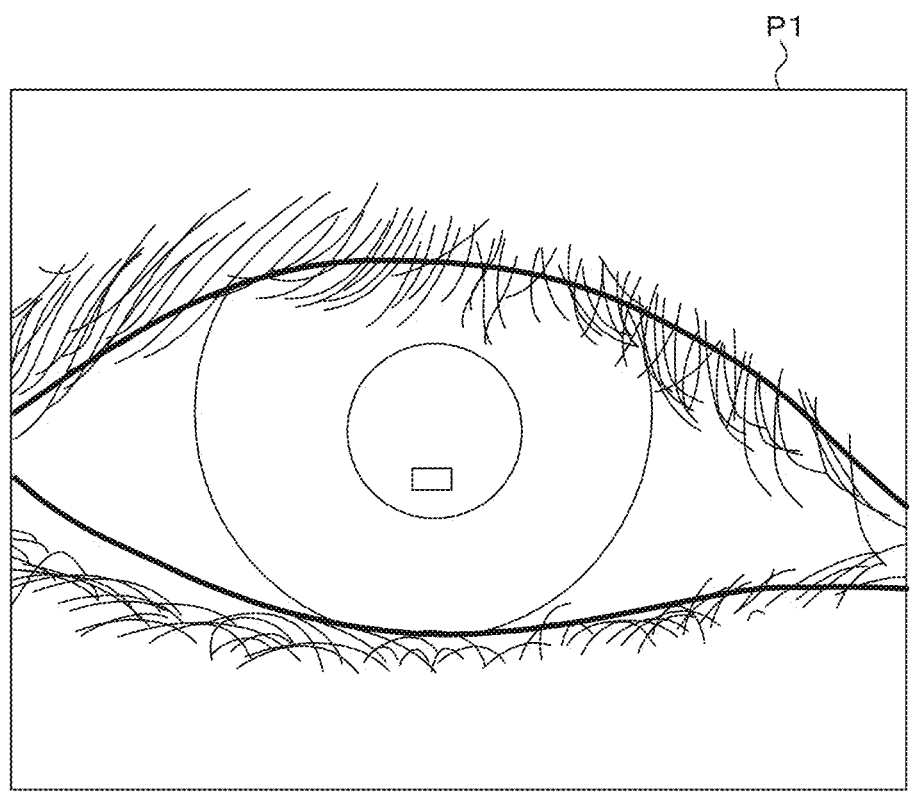
FIG. 3 shows an image that is a simplification of a digital image.

The image P1 shown in FIG. 3 is an image in which the digital image P has been simplified by showing an outline of the iris and the part surrounding this with lines alone. For convenience, the explanation below uses the digital image P and as necessary uses the image P1 corresponding to this digital image P.

Returning to FIG. 1, the comparison apparatus has a reference pixel setting unit 31, a pupil center position determining unit 32, an iris image determining unit 33, an annular region specifying unit 34, a microregion specifying unit 35, an average luminance calculating unit 36, a characteristic curve generating unit 37, a code generating unit 38 and a comparison unit 39.

Figure 4:
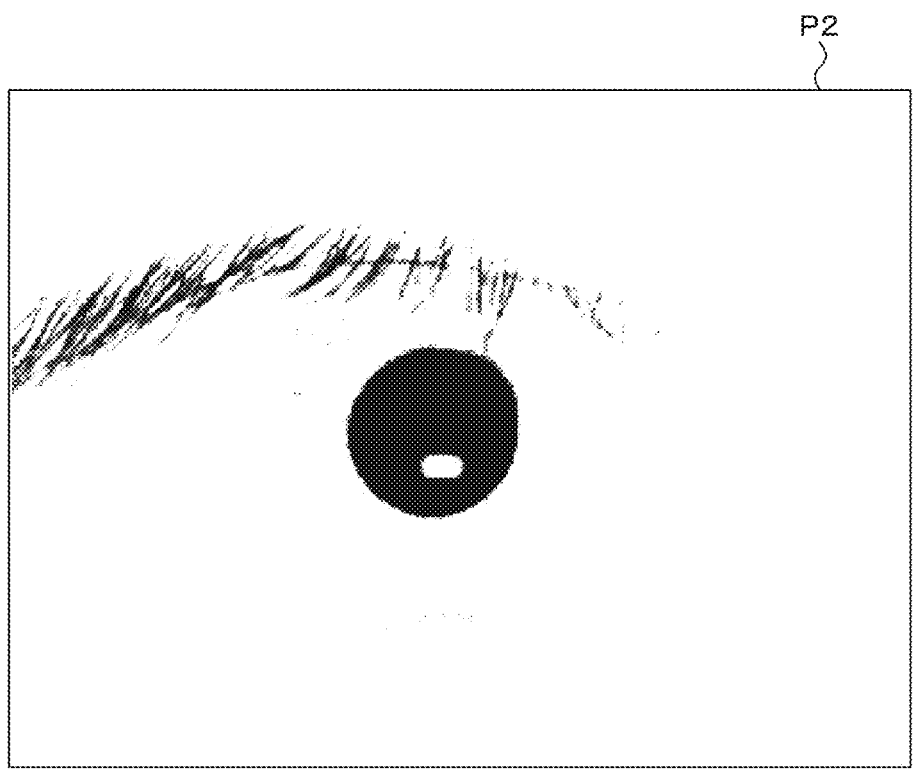
FIG. 4 shows a binary image.

The reference pixel setting unit 31 first extracts low-luminance pixels having a luminance below a prescribed value from among multiple pixels comprising the digital image P output from the image capturing device 10. Extraction of low-luminance pixels is accomplished for example by converting the digital image P into a binary image and extracting pixels whose apparent luminance at this time is 0. As one example, FIG. 4 shows a binary image P2 obtained through image conversion of the digital image P using a prescribed threshold value. The reference pixel setting unit 31 extracts the low-luminance pixels comprising the black parts of the binary image shown in FIG. 4. The threshold value used by the reference pixel extracting unit 31 can be determined based on the shooting conditions or the like for the digital image P. In this embodiment, this threshold value is determined such that in the binary image P2 pixels comprising the image of the iris appear as high-luminance pixels and pixels comprising the image of the pupil appear as low-luminance pixels. By determining the threshold value in this manner, in the binary image P2 the pixels comprising the image of the pupil and the eyelashes in particular appear as low-luminance pixels.

Next, the reference pixel setting unit 31 successively selects extracted low-luminance pixels and appends for example the value 1 to each of the multiple pixels within a prescribed distance from the selected low-luminance pixel. Below, the operation of the reference pixel setting unit 31 is explained with reference to FIG. 5, which shows a sample image SAMP1.

Figure 5:
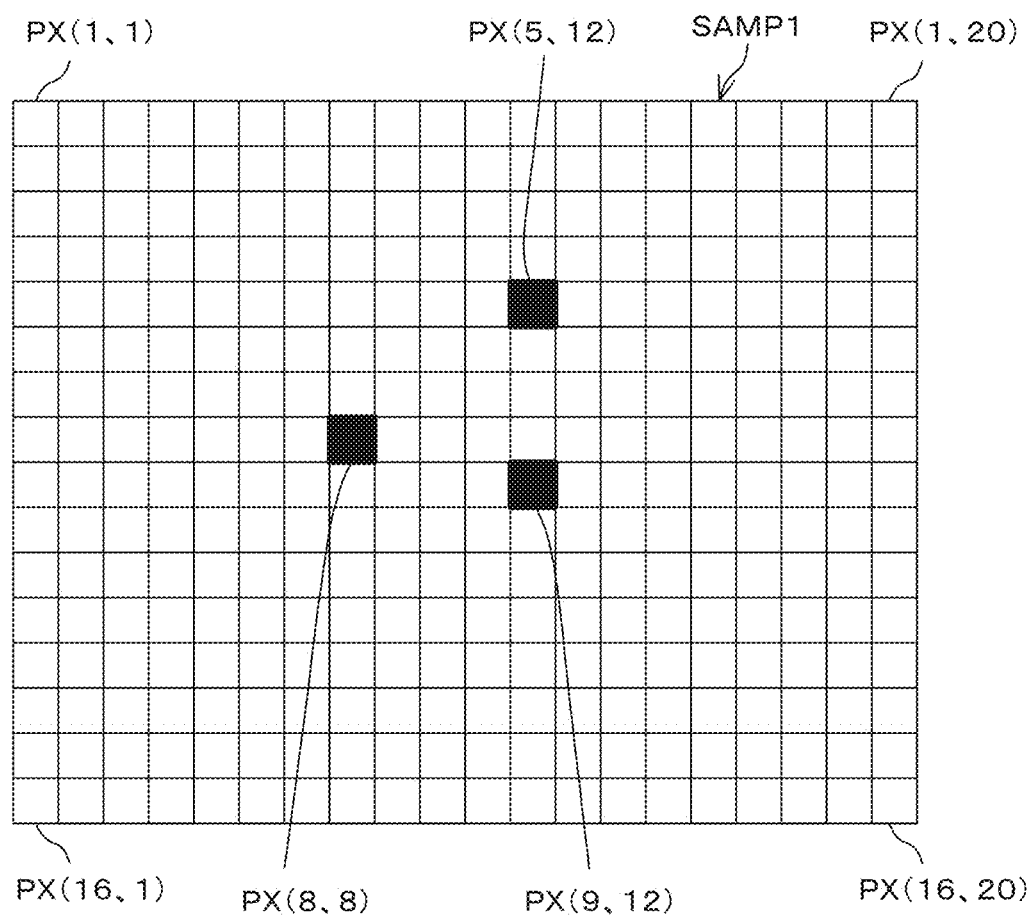
FIG. 5 shows a sample image.
Figure 6A:
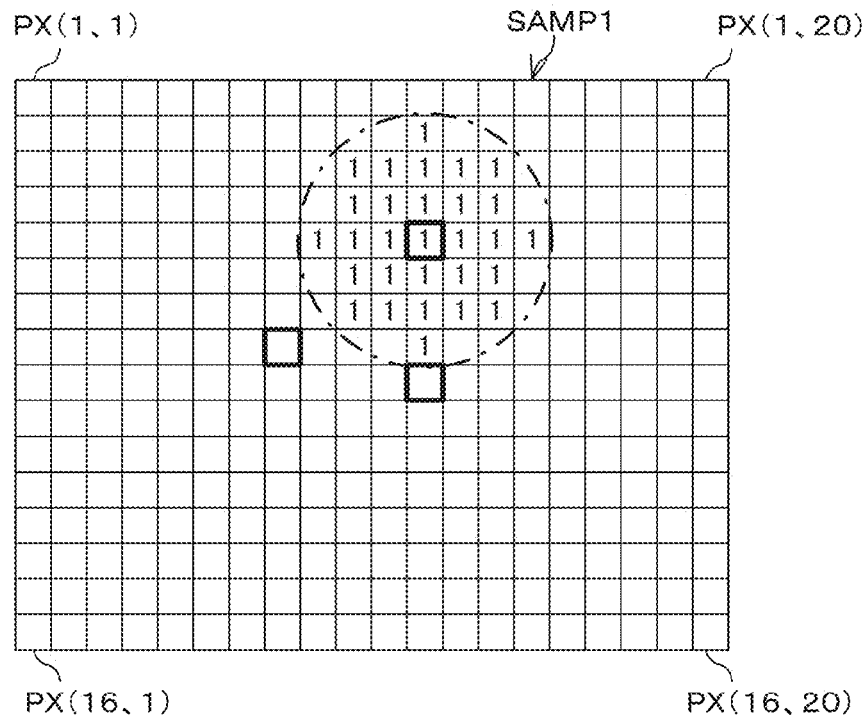
FIG. 6A is a drawing (part 1) for explaining the operation of a reference pixel setting unit.
Figure 6B:
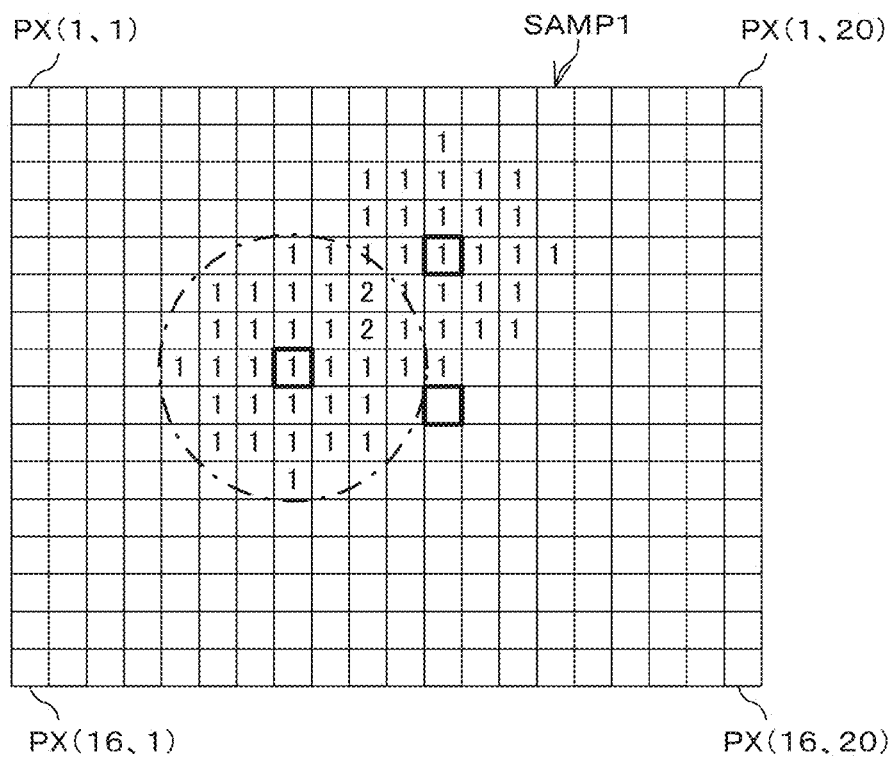
FIG. 6B is a drawing (part 2) for explaining the operation of a reference pixel setting unit.
Figure 7:
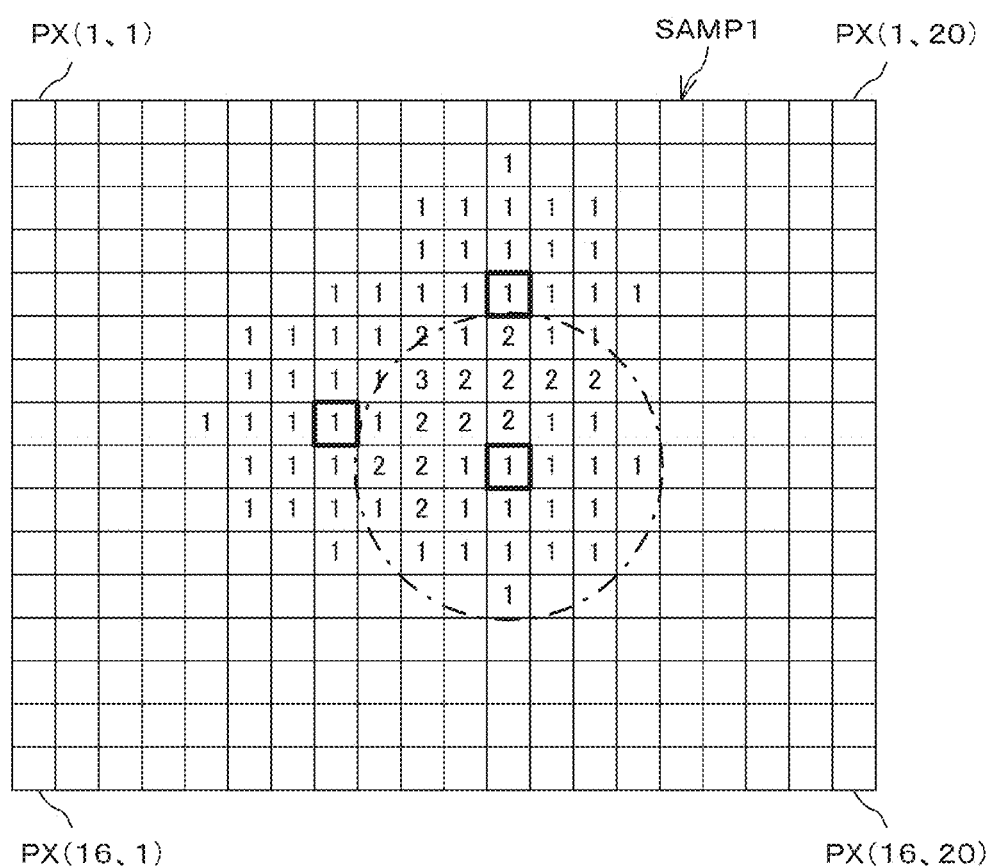
FIG. 7 is a drawing (part 3) for explaining the operation of a reference pixel setting unit.

As shown in FIG. 5, the sample image SAMP1 is an image composed of pixels PX(m,n) arranged in a matrix of 16 rows and 20 columns, as one example. Here, m is an integer from 1 to 16 indicating the row number, and n is an integer from 1 to 20 indicating the column number. This image SAMP1 is a binary image composed of three low-luminance pixels PX(5, 12), PX(8,8) and PX(9,12) and high-luminance pixels PX other than this, and the three low-luminance pixels PX(5,12), PX(8,8) and PX(9,12) are extracted by the reference pixel setting unit 31. The reference pixel setting unit 31 first selects the low-luminance pixel PX(5,12) in the fifth row. Furthermore, as can be seen by referring to FIG. 6A, the reference pixel setting unit 31 appends a 1 to the low-luminance pixel PX(5,12) and to each of the pixels PX(m,n) within a prescribed distance from this low-luminance pixel PX(5,12).

Next, the reference pixel setting unit 31 selects the low-luminance pixel PX(8,8) in the eighth row. As can be seen by referring to FIG. 6B, the reference pixel setting unit 31 appends a 1 to this low-luminance pixel PX(8,8) and to the pixels PX(m,n) within a prescribed distance from this low-luminance pixel PX(8,8). Here, the pixel PX(6,10) in the sixth row and the pixel PX(7,10) in the seventh row are within the prescribed distance from both the low-luminance pixel PX(5, 12) and the low-luminance pixel PX(8,8). Hence, the reference pixel setting unit 31 sums the values appended thus far to these pixels PX(6,10) and PX(7,10). When this process has been completed, the sum of the appended values is 2 at the pixels PX(6,10) and PX(7,10).

Next, the reference pixel setting unit 31 selects the low-luminance pixel PX(9,12) in the ninth row. As can be seen by referring to FIG. 7, the reference pixel setting unit 31 appends a 1 to this low-luminance pixel PX(9,12) and to the pixels PX(m,n) within a prescribed distance from this low-luminance pixel PX(9,12). Here, the pixel PX(7,10) in the seventh row is within the prescribed distance from each of the low-luminance pixels PX(5,12), PX(8,8) and PX(9,12). Hence, the reference pixel setting unit 31 sums the values appended thus far to this pixel PX(7,10). When this process has been completed, the sum of the appended values is 3 at the pixel PX(7,10). The reference pixel setting unit 31 executes the above-described process for all of the low-luminance pixels contained in the image. Through this, the sum of appended values is computed for each of the pixels PX(m,n).

Figure 8:
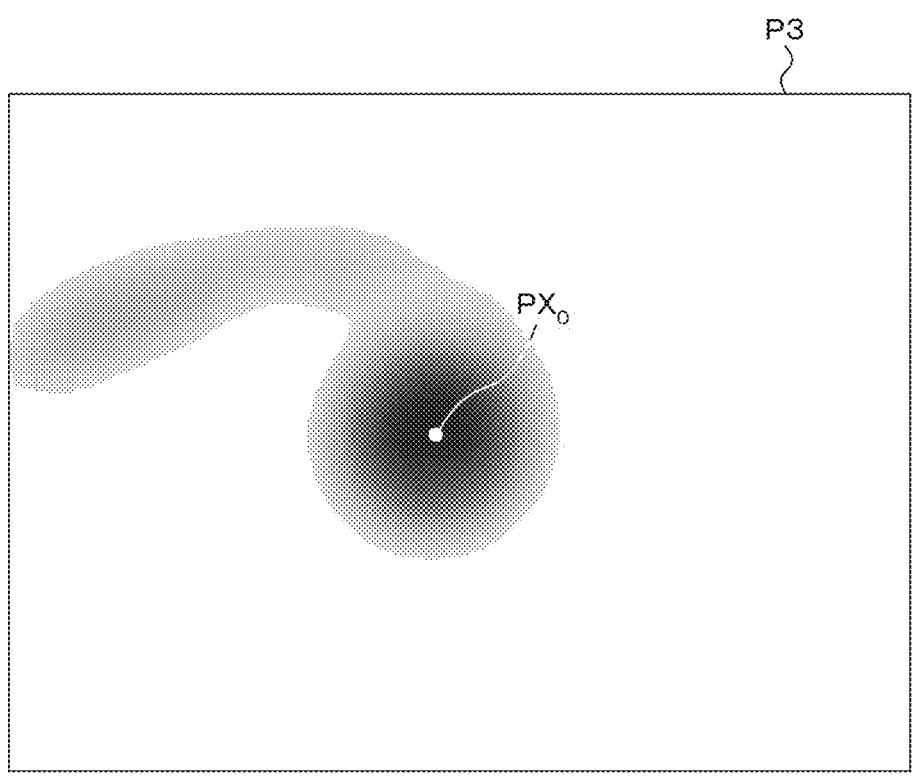
FIG. 8 shows an image obtained through processing by the reference pixel setting unit.

The reference pixel setting unit 31 executes the above-described process for each of the low-luminance pixels comprising the binary image P2. FIG. 8 shows an image P3 that is one example of an image conceptually showing the results of the reference pixel setting unit 31 accomplishing the above-described process for the low-luminance pixels comprising the black part of the binary image P2. In the image P3, pixels with larger summed appended values are shown colored with the higher densities.

Figure 9:
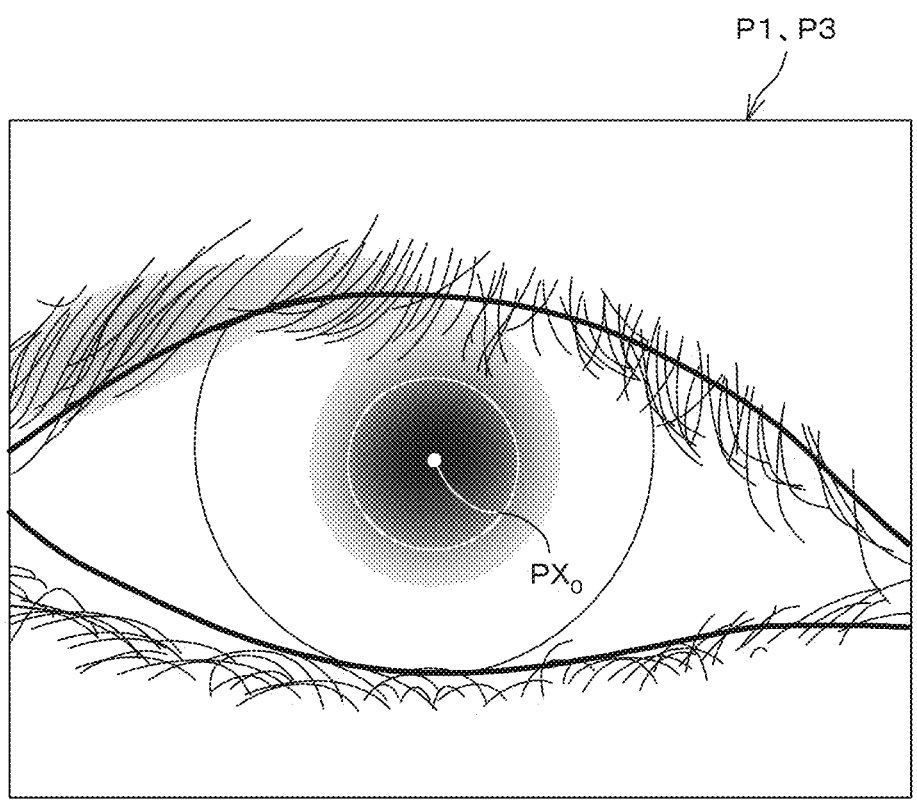
FIG. 9 shows an image for explaining the processing results of the reference pixel setting unit.

Furthermore, the reference pixel setting unit 31 sets the pixel with the largest appended summed value as the reference pixel $PX_0$, and outputs the position information of this reference pixel $PX_0$ to the pupil center position determining unit 32. This reference pixel $PX_0$ matches the position of the pixel with the highest density in the image P3, as shown in FIG. 8. In addition, FIG. 9 shows an image (that is to say, an image for explaining the processing results of the reference pixel setting unit 31) in which the image P1 (see FIG. 3) and the image P3 (see FIG. 8) are shown superimposed. As shown in FIG. 9, the position of the reference pixel $PX_0$ substantially matches the center of the pupil of the eye shown in the image P1.

Figure 10:
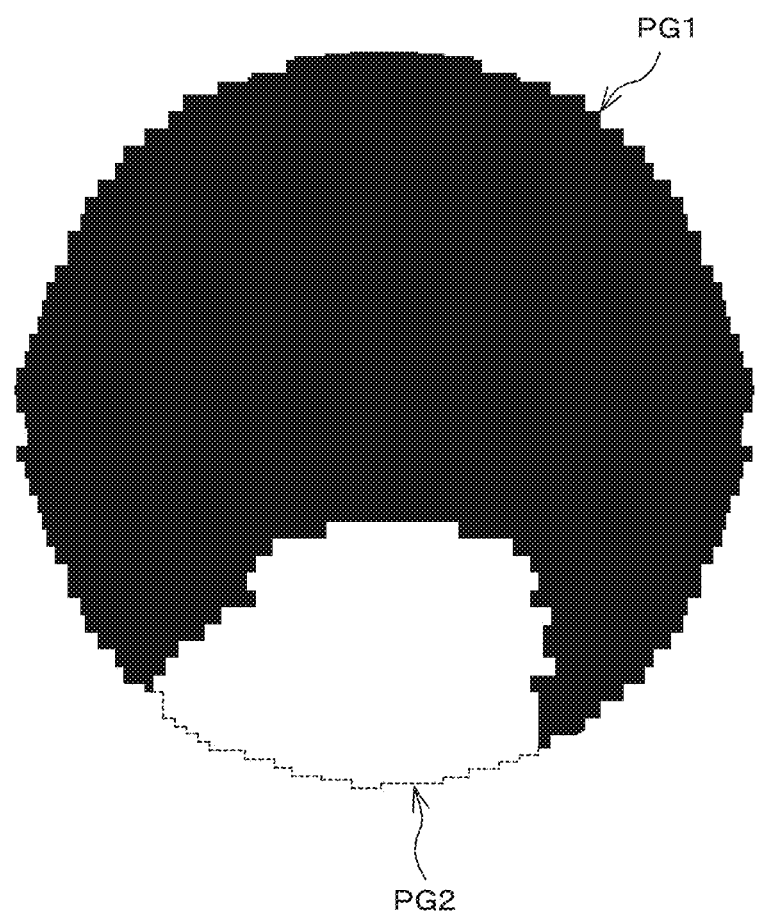
FIG. 10 shows a low-luminance pixel group and a high-luminance pixel group comprising a pupil.

However, normally when the image of an eye including the pupil is shot, the luminance of a portion of the pixels out of the pixels comprising the pupil becomes larger due to the influence of light reflected by the surface of the cornea. Through this, the pixel group comprising the pupil appearing in the binary image P2 is divided into a low-luminance pixel group PG1 and a high-luminance pixel group PG2. FIG. 10 shows one example of the low-luminance pixel group PG1 and the high-luminance pixel group PG2 comprising the pupil contained in the binary image P2. As is clear from FIG. 10, with the present invention the high-luminance pixel group PG2 is unevenly distributed among the pixels comprising the image of the pupil, so as the number of pixels comprising the high-luminance pixel group PG2 increases, it is conceivable that the position of the reference pixel $PX_0$ could shift gradually from the center of the pupil. Hence, the pupil center position determining unit 32 detects the center position of the pupil on the basis of the distribution of the low-luminance pixel group PG1 comprising the pupil in the binary image P2 and the position information of the reference pixel $PX_0$.

Figure 11:
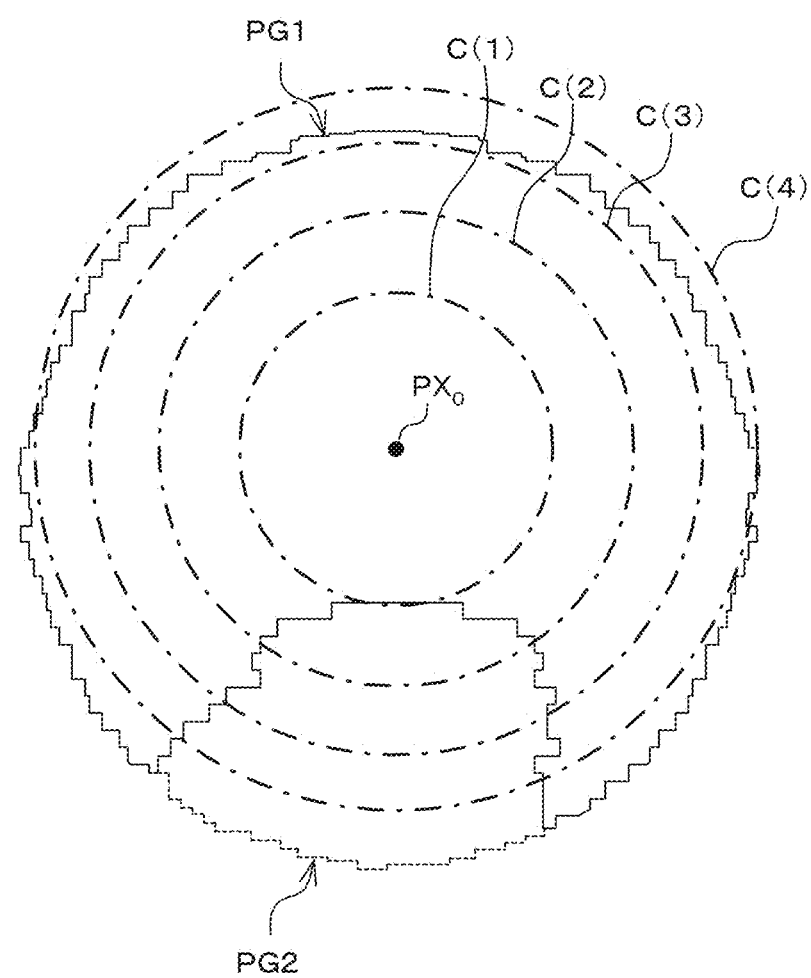
FIG. 11 is a drawing (part 1) for explaining the operation of a pupil center position determining unit.

As shown in FIG. 11, the pupil center position determining unit 32 establishes a circle C(1) centered at the reference pixel $PX_0$. The radius r(1) of this circle C(1) is established so as to be sufficiently small compared to the radius of the pupil. For example, the radius r(1) of the circle C(1) is preferably determined by taking into consideration the distribution range of the low-luminance pixel group PG1 in the x-axis direction or the y-axis direction.

Next, the pupil center position determining unit 32 establishes a circle C(2) centered at the reference pixel $PX_0$ and having a radius larger than the radius r(1) of the circle C(1).

Next, the pupil center position determining unit 32 computes the areas $S_1$ and $S_2$ of the circles C(1) and C(2), respectively, and the number $N_1$ and $N_2$ of low-luminance pixels inside the circles C(1) and C(2), respectively. Furthermore, the pupil center position determining unit 32 computes a ratio $R_1$ of the number $(N_2-N_1)$ of low-luminance pixels inside the circles C(1) and C(2), respectively, to the difference $(S_2-S_1)$ in surface area between the circle C(1) and the circle C(2). In other words, $R_1=(N_2-N_1)/(S_2-S_1)$.

Next, the pupil center position determining unit 32 determines whether or not the computed ratio $R_1$ is at least a prescribed value. Furthermore, when this determination is in the affirmative, the pupil center position determining unit 32 establishes a circle C(3) having a radius larger than the radius of the circle C(2). Furthermore, the pupil center position determining unit 32 computes the areas $S_2$ and $S_3$ of the circles C(2) and C(3), respectively, and the number $N_2$ and $N_3$ of low-luminance pixels inside the circles C(2) and C(3), respectively. Furthermore, the pupil center position determining unit 32 computes a ratio $R_2$ of the number $(N_3-N_2)$ of low-luminance pixels inside the circles C(2) and C(3), respectively, to the difference $(S_3-S_2)$ in surface area between the circle C(2) and the circle C(3). In other words, $R_2=(N_3-N_2)/(S_3-S_2)$.

Next, the pupil center position determining unit 32 determines whether or not the computed ratio $R_2$ is at least a prescribed value. The above-described process is then repeatedly executed until a ratio $R_N$ no greater than the prescribed value is computed. During this repetition, the sizes of the two circles defined on the image of the pupil in the binary image P2 gradually enlarge. The above-described ratios $R_1$, $R_2$, ..., shall collectively be called $R_N$ (N=1, 2, ...).

When a ratio $R_N$ no greater than the prescribed value is computed during this repetition, the pupil center position determining unit 32 specifies the center position of the pupil using the circle C(N) at that time. Hence, the explanation below is for the case in which the circles C(1), C(2) and C(3) are contained within the region stipulated by the low-luminance pixel group PG1 and the high-luminance pixel group PG2 but the circle C(4) protrudes from this region.

The circles C(1), C(2) and C(3) contain only pixels comprising the pupil and belonging to either the low-luminance pixel group PG1 or the high-luminance pixel group PG2, so the computed ratios $R_1$ and $R_2$ are substantially constant. In contrast, the circle C(4) contains pixels other than pixels belonging to the low-luminance pixel group PG1 or the high-luminance pixel group PG2 comprising the pupil. These pixels are high-luminance pixels comprising the image of the iris. Consequently, the number $N_4$ of low-luminance pixels contained inside the circle C(4) declines, and as a result, the value of the computed ratio $R_3$ $(=(N_4-N_3)/(S_4-S_3))$ becomes smaller than the prescribed value.

Figure 12:
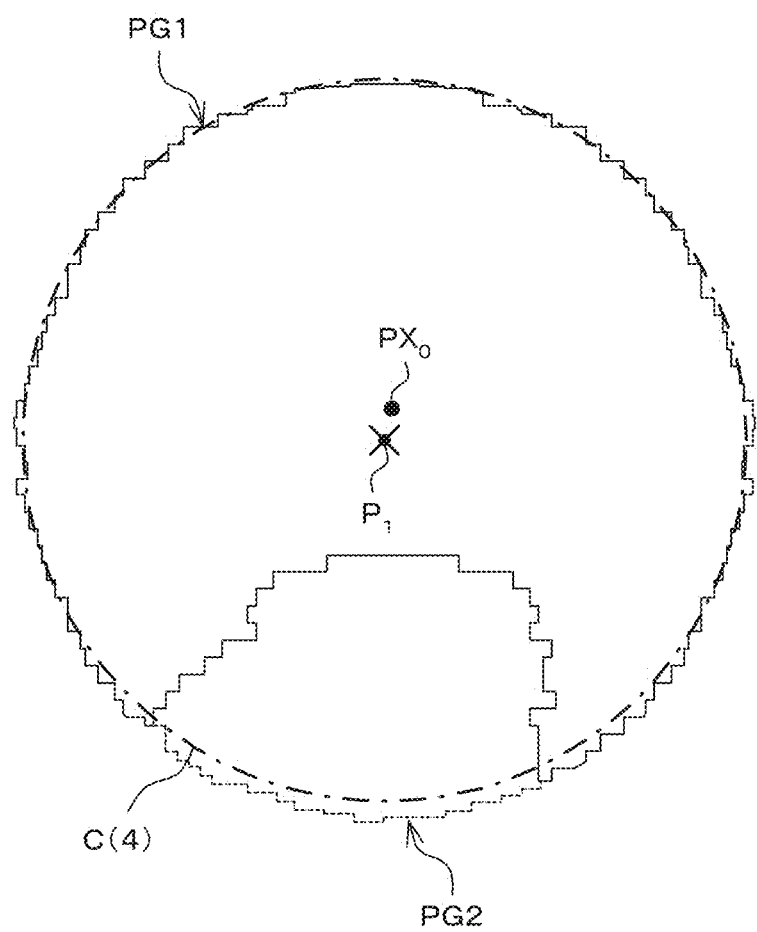
FIG. 12 is a drawing (part 2) for explaining the operation of a pupil center position determining unit.

Next, the pupil center position determining unit 32 searches for the center position P1 of the circle C(4) when the number of low-luminance pixels contained in the circle C(4) is a maximum, while moving the circle C(4) with the reference pixel $PX_0$ as a reference position, as can be seen by referring to FIG. 12. Furthermore, the pupil center position determining unit 32 specifies the searched position $P_1$ as the position of the pupil center.

The radiuses of the circles C(1) to C(N) are preferably set so as to differ by only one pixel to several pixels, for example, with the size of a pixel as a reference, for example. The smaller the difference between the radius of the circle C(N−1)

and the radius of the circle C(N) is, the more accuracy is improved in detecting the pupil center.

Figure 13:
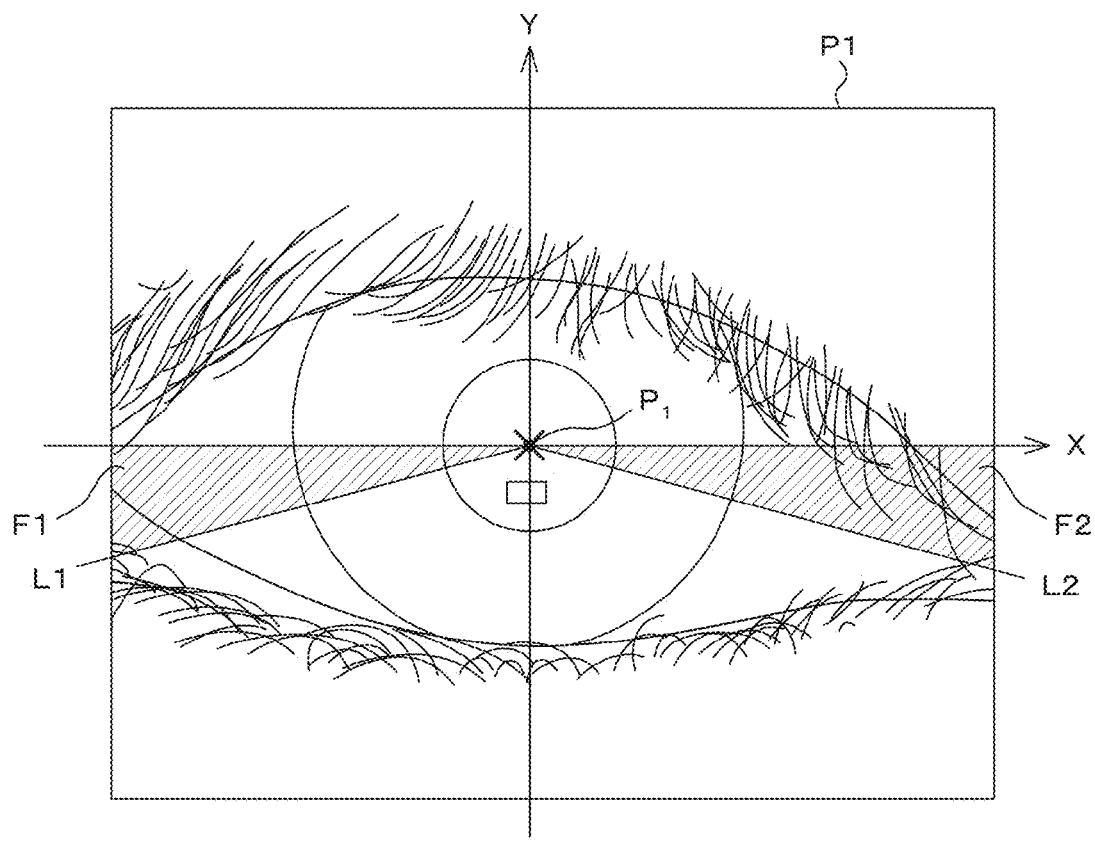
FIG. 13 is a drawing (part 1) for explaining the operation of an iris image determining unit.
Figure 14A:
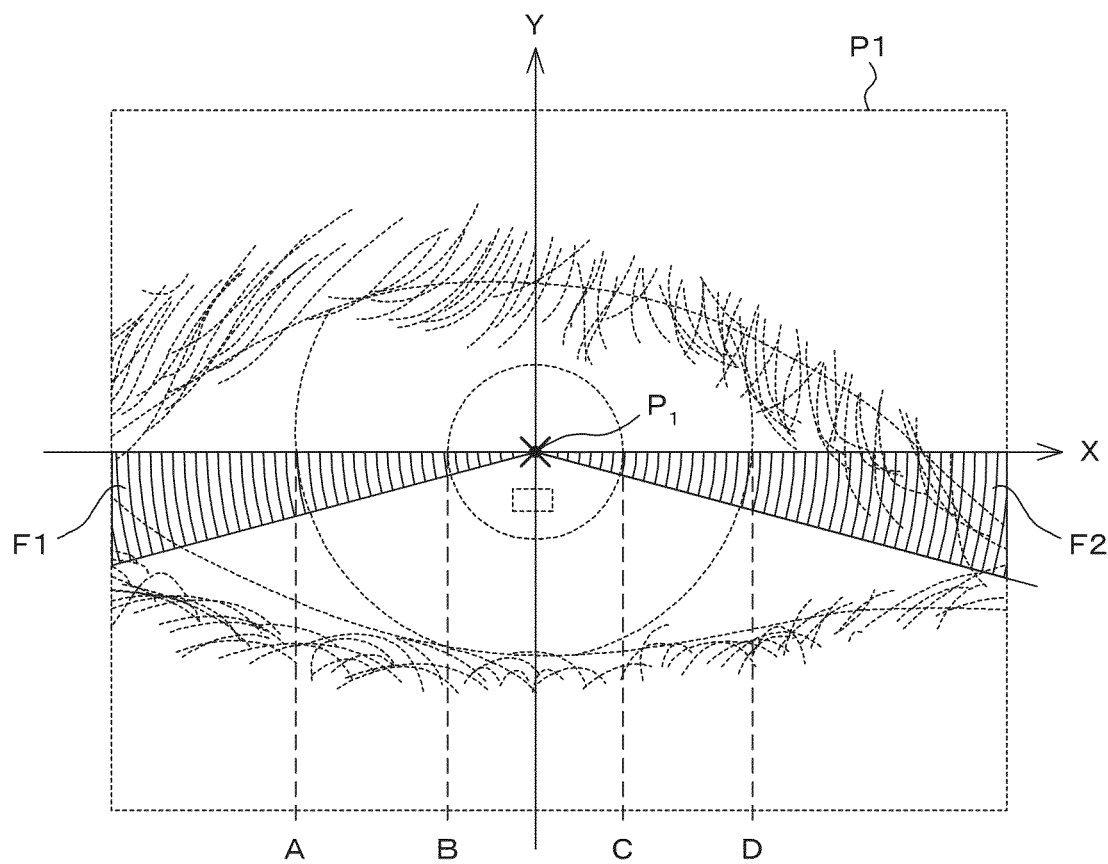
FIG. 14A is a drawing (part 2) for explaining the operation of an iris image determining unit.

The aforementioned iris image determining unit 33 defines an x-y coordinate system with the origin at the position $P_1$ on the image P1, as shown in FIG. 13. With this coordinate system, the x-axis extends in the horizontal direction (the sideways direction). Furthermore, the iris image determining unit 33 prescribes triangular regions F1 and F2 starting at the position $P_1$ on the image P1 and defined by lines L1 and L2, each forming angles of 15 degrees with the x-axis. Next, the iris image determining unit 33 establishes multiple arc-shaped microregions by partitioning the region F1 using multiple arcs with the angle defined by the x-axis and the line L1 as the central angle, as shown in FIG. 14A. In addition, the iris image determining unit 33 establishes multiple arc-shaped microregions by partitioning the region F2 using multiple arcs with the angle defined by the x-axis and the line L2 as the central angle.

Figure 14B:
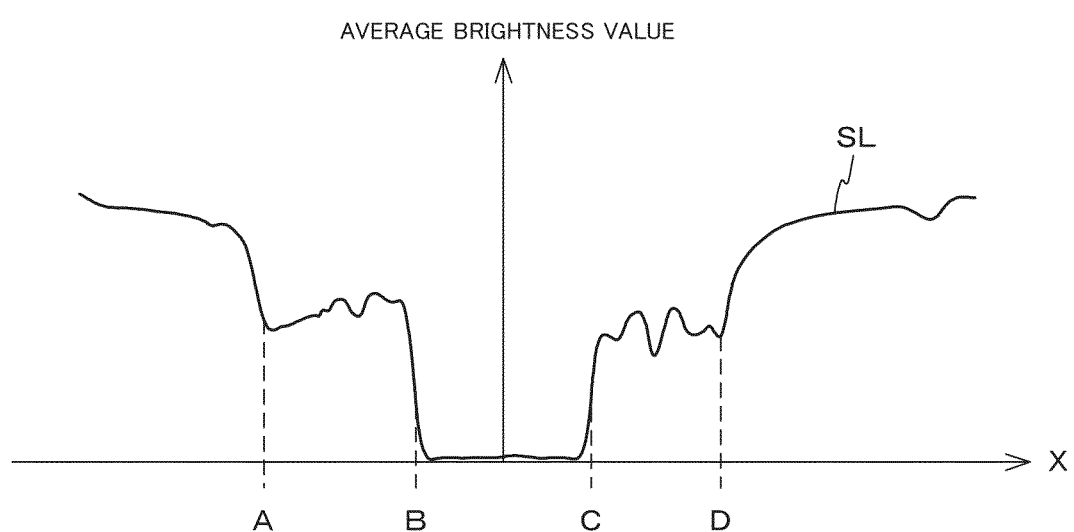
FIG. 14B shows a characteristic curve.

FIG. 14B shows a characteristic curve SL indicating the relationship between a position x and the average value of the luminance of the arc-shaped microregions. The iris image determining unit 33 computes the average value of the luminance of the pixels contained in a microregion for each microregion belonging to region F1 or region F2. Furthermore, the iris image determining unit 33 computes the characteristic curve SL expressing the relationship between the position of the microregion on the x-axis and the average value of the corresponding luminance. Next, the iris image determining unit 33 finds the x-coordinates A and D at the intersection of the x-axis and the outer edge of the iris on the basis of the degree of change in this characteristic curve SL.

The x-coordinates A and D at the intersection points can be specified by comparing the derivative obtained by differentiating the characteristic curve SL at the position x on the x-axis with a prescribed threshold value, for example. As can be seen by referring to the characteristic curve SL in FIG. 14B, in general continuity can be observed in the degree of change in the average value of the luminance at the boundary between the iris region and the white of the eye. In addition, in the region where the change is made from the iris region to the eye-white region, the degree of change in the average value of the luminance is larger than in other areas. By using this property, the x-coordinates A and D at the intersection of the x-axis and the outer edge of the iris can be found substantially accurately using the derivative of the characteristic curve SL. The x-coordinates B and C are the intersections points of the x-axis and the outer edge of the pupil.

Figure 15:
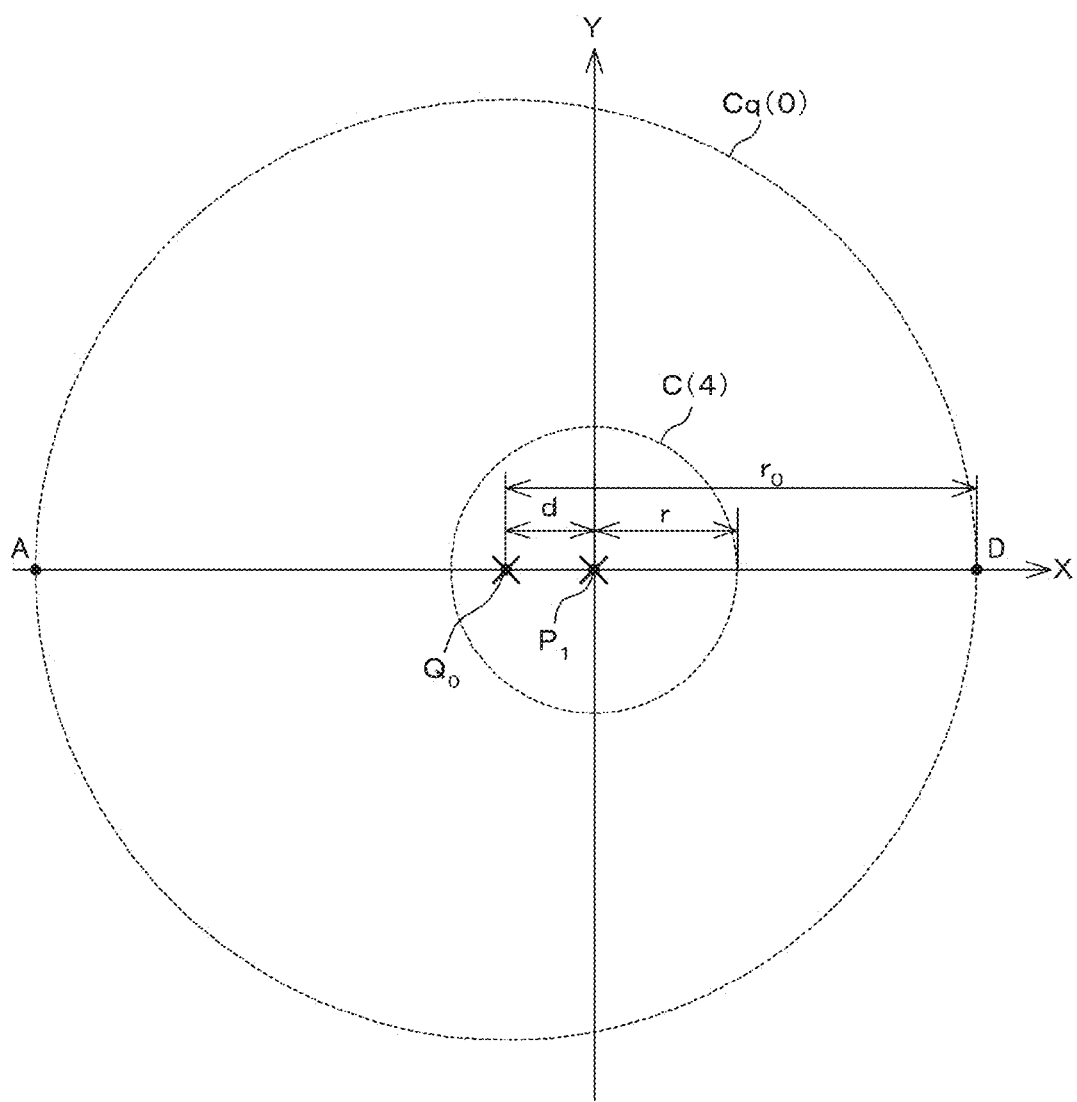
FIG. 15 is a drawing (part 1) for explaining the operation of an annular region specifying unit.

As shown in FIG. 15, consider for example a circle Cq(0) whose center is positioned on the x-axis and whose circumference passes through point (A,0) and point (D,0) in the x-y coordinate system. The circle Cq(0) is a circle having a center $Q_0$ at a point ((A+D)/2,0) and a radius of (D−A)/2. The circle Cq(0) substantially matches the outer edge of the iris, and the circle C(4) substantially matches the outer edge of the pupil. Hence, by finding the x-coordinates A and D, the iris image determining unit 33 specifies as the region where the iris image exists a region defined by the circle C(4) and the circle Cq(0) centered at a position $P_1$ on the image P1. Furthermore, the iris image determining unit 33 passes the specified results to the annular region specifying unit 34.

As shown in FIG. 15, the center $P_1$ of the circle C(4) substantially matching the outer edge of the pupil and the center $Q_0$ of the circle Cq(0) substantially matching the outer edge of the iris in general do not match. This is because even when the eye is photographed from the front of the target individual, the optical axis of the lens (unrepresented) of the image capturing device 10 and the line of sight are not parallel because the line of sight of a person's left and right eyes are in general not parallel due to parallax. Because the iris has a spherical shape, the center of the iris and the center of the pupil are shifted on the digital image P photographed by the image capturing device 10, the optical axis of the lens of which is inclined with respect to the line of sight.

Figure 16:
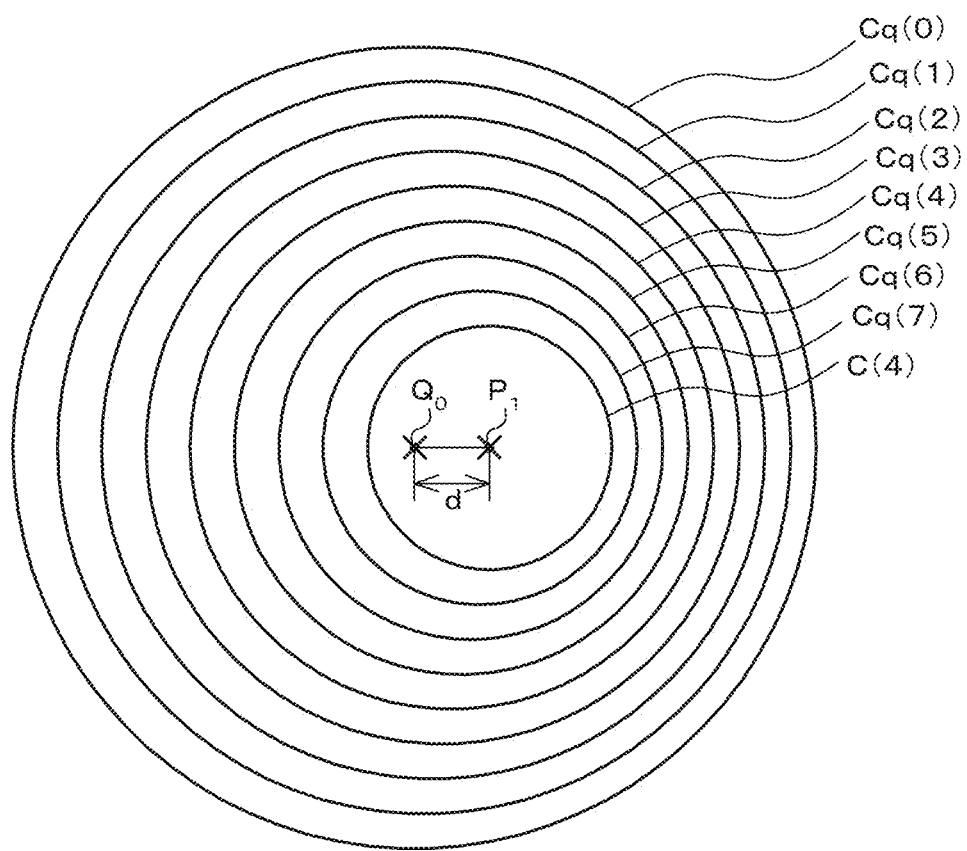
FIG. 16 is a drawing (part 2) for explaining the operation of an annular region specifying unit.
Figure 17:
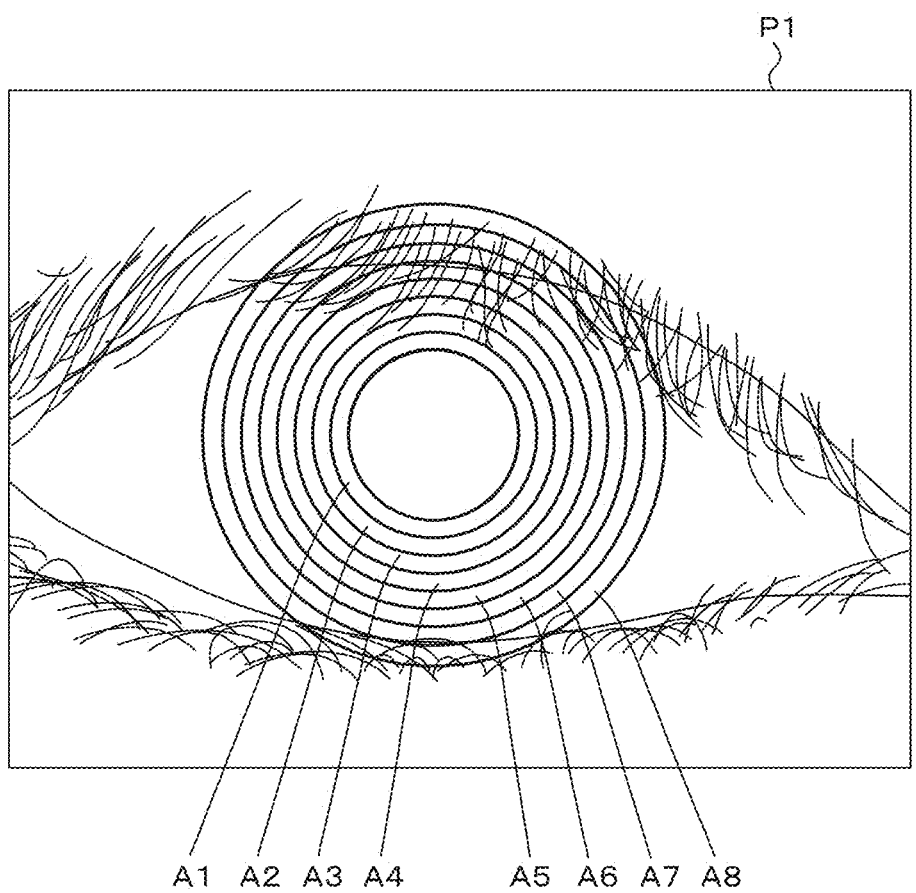
FIG. 17 is a drawing (part 3) for explaining the operation of an annular region specifying unit.

The annular region specifying unit 34 takes the above circumstances into consideration and partitions the region defined by the circle C(4) substantially matching the outer edge of the pupil and the circle Cq(0) substantially matching the outer edge of the iris into eight annular regions using seven circles Cq(1) to Cq(7), as shown in FIG. 16. This action is fundamentally described below.

First, the annular region specifying unit 34 measures the distance d between the center $P_1$ of the circle C(4) and the center $Q_0$ of the circle Cq(0). In addition, the annular region specifying unit 34 computes the centers $Q_1$ to $Q_7$ of the circles Cq(1) to Cq(7) by repeatedly adding to the x-coordinate of the center $Q_0$ a value found by dividing the distance d by 8. The coordinates of the centers $Q_1$ to $Q_7$ are respectively computed as $Q_1$ ((A+D)/2+d/8,0), $Q_2$ ((A+D)/2+d/4,0), $Q_3$ ((A+D)/2+3d/8,0), $Q_4$ ((A+D)/2+d/2,0), $Q_5$ ((A+D)/2+5d/8,0), $Q_6$ ((A+D)/2+3d/4,0), $Q_7$ ((A+D)/2+7d/8,0).

Next, the annular region specifying unit 34 computes the radiuses $r_1$ to $r_7$ of the circles Cq(1) to Cq(7) by subtracting from the radius $r_0$ of the circle Cq(0) a value found by dividing the difference between the radius (taken to be r) of the circle C(4) and the radius $r_0$ of the circle Cq(0) by 8. The radiuses $r_1$ to $r_7$ are respectively computed as $r_1$: $(r_0-(r_0-r)/8)$, $r_2$: $(r_0-2\cdot(r_0-r)/8)$, $r_3$: $(r_0-3\cdot(r_0-r)/8)$, $r_4$: $(r_0-4\cdot(r_0-r)/8)$, $r_5$: $(r_0-5\cdot(r_0-r)/8)$, $r_6$: $(r_0-6\cdot(r_0-r)/8)$, $r_7$: $(r_0-7\cdot(r_0-r)/8)$.

Next, the annular region specifying unit 34 defines the seven circles Cq(1) to Cq(7) in the region defined by the circles Cq(0) and Cq(4) as shown in FIG. 16 on the basis of the computation results relating to the centers $Q_1$ to $Q_7$ and the radiuses $r_1$ to $r_7$ computed as described above. Through this, the image of the iris contained in the image P1 is partitioned into eight annular regions A1 to A8 by the seven circles Cq(1) to Cq(7), as can be seen by referring to FIG. 17. Furthermore, the annular region specifying unit 34 outputs information relating to the eight annular regions A1 to A8 to the microregion specifying unit 35.

The microregion specifying unit 35 partitions each of the eight annular regions A1 to A8 into 256 microregions. More specifically, the circumferences of the circle C(4) and the circles Cq(1) to Cq(7) are divided into 256 arcs with equal center angles. Furthermore, each of the microregions is generated by defining an arc of one circle (for example, the circle C(4)), a set of arcs formed by the arc in a corresponding relationship to the above-described arc in the circle (for example, the circle Cq(7)) adjacent to that circle, and line segments connecting the end points of the two arcs. A method of generating the microregions is fundamentally described below with reference to FIG. 18.

Figure 18:
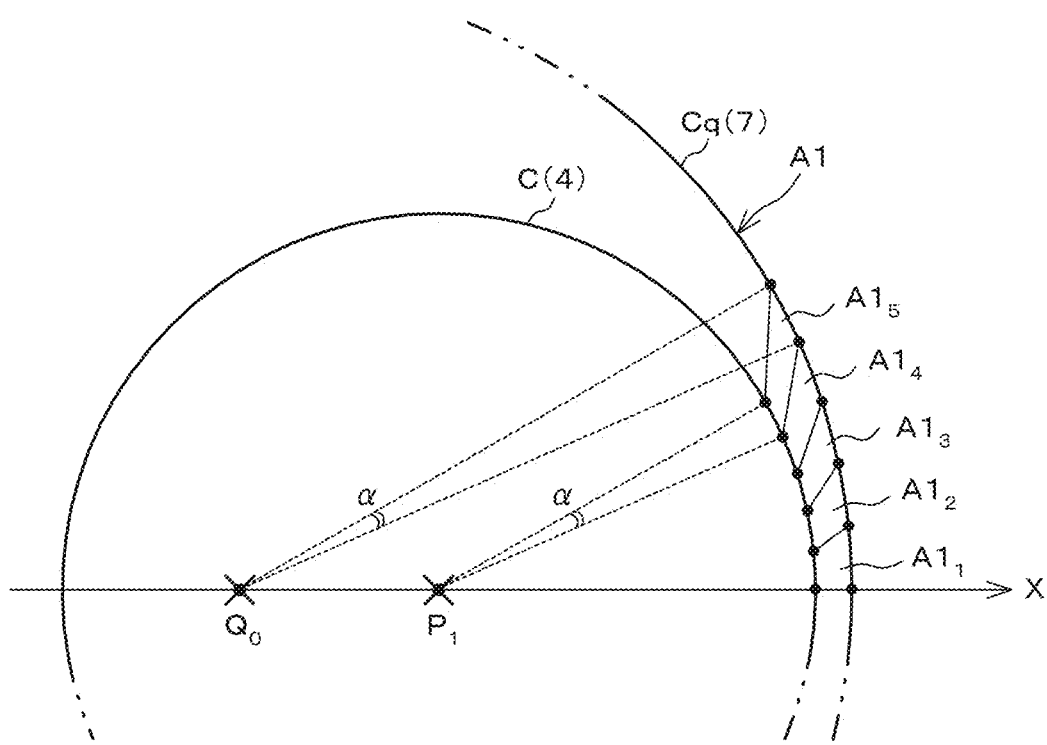
FIG. 18 is a drawing for explaining the operation of a microscopic region specifying unit.

FIG. 18 shows the state with the annular region A1 defined by the circle C(4) and the circle Cq(7) partitioned into 256 microregions. As shown in FIG. 18, the microregion specifying unit 35 divides the circle C(4) and the circle Cq(7) each into arcs whose central angle is α (360/256) with the intersection points between each of the arcs and the x-axis as reference points, and partitions the annular region A1 into 256 microregions $A1_1$ to $A1_{256}$ by defining line segments connecting the end points of arcs having a corresponding relationship. Similarly, the microregion specifying unit 35 partitions the annular regions A2 to A8 into microregions $A2_1$ to $A2_{256}$, microregions $A3_1$ to $A3_{256}$, microregions $A4_1$ to $A4_{256}$, microregions $A5_1$ to $A5_{256}$/microregions $A6_1$ to $A6_{256}$, microregions $A7_1$ to $A7_{256}$, and microregions $A8_1$ to $A8_{256}$, respectively. Furthermore, the microregion specifying unit 35 outputs information relating to the above-described microregions to the average luminance calculating unit 36.

The average luminance calculating unit 36 first finds the average value $AVG1_i$ of the luminance of pixels contained in the microregions $A1_i$ (i=1, 2, . . . , 256) for each of the microregions $A1_1$ to $A1_{256}$ belonging to the annular region A1. Next, the average luminance calculating unit 36 finds the average value $AVG2_i$ of the luminance of pixels contained in the each of the microregions $A2_i$ belonging to the annular region A2. Next, the average luminance calculating unit 36 finds the average value $AVG3_i$ of the luminance of pixels contained in the each of the microregions $A3_i$ belonging to the annular region A3. Next, the average luminance calculating unit 36 finds the average value $AVG4_i$ of the luminance of pixels contained in the each of the microregions $A4_i$ belonging to the annular region A4. Next, the average luminance calculating unit 36 finds the average value $AVG5_i$ of the luminance of pixels contained in the each of the microregions $A5_i$ belonging to the annular region A5. Next, the average luminance calculating unit 36 finds the average value $AVG6_i$ of the luminance of pixels contained in the each of the microregions $A6_i$ belonging to the annular region A6. Next, the average luminance calculating unit 36 finds the average value $AVG7_i$ of the luminance of pixels contained in the each of the microregions $A7_i$ belonging to the annular region A7. Next, the average luminance calculating unit 36 finds the average value $AVG8_i$ of the luminance of pixels contained in the each of the microregions $A8_i$ belonging to the annular region A8. Furthermore, the average luminance calculating unit 36 outputs information relating to the above-described average values to the characteristic curve generating unit 37.

Figure 19A:
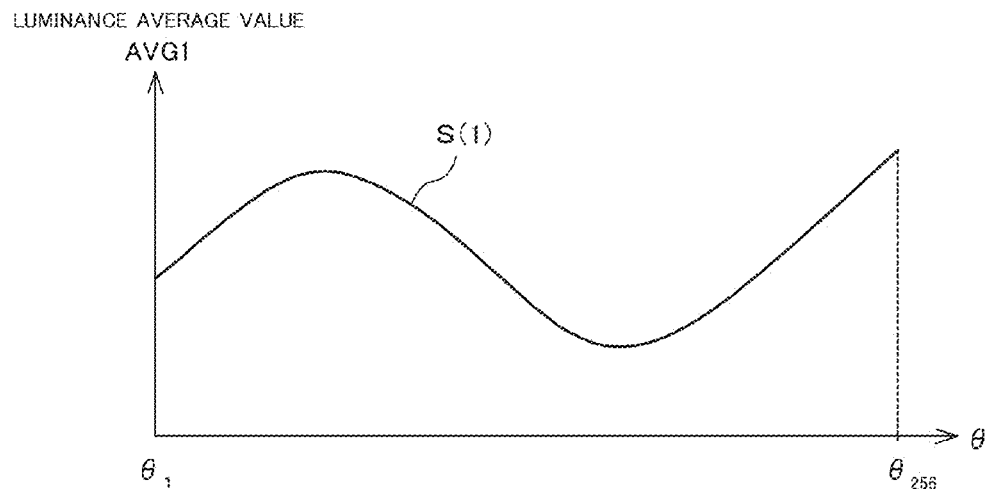
FIG. 19A shows a characteristic curve line S(1).

FIG. 19A shows a characteristic curve S(1) expressing the relationship between the polar coordinates of the microregions $A1_i$ and the average value of the luminance computed for each of the microregions $A1_i$. The characteristic curve generating unit 37 first plots points determined by the average value $AVG1_1$ computed for each of the microregions $A1_i$ and the polar coordinates $\theta_i$ of the microregions $A1_i$ on coordinates with the horizontal axis being the polar coordinate and the vertical axis being the luminance. Furthermore, a curve connecting these points is generated as the characteristic curve S(1). The action of the characteristic curve generating unit 37 is fundamentally described below.

For example, the values of the polar coordinates $\theta_i$ of the microregions $A1_i$ are indicated by $(i-1) \cdot \alpha$, as shown in FIG. 18. Accordingly, the values of the polar coordinates $\theta_i$ of the microregions $A1_i$ are determined such that the value of the polar coordinate $\theta_1$ of the microregion $A1_1$ is 0, the value of the polar coordinate $\theta_2$ of the microregion $A1_2$ is $\alpha$, the value of the polar coordinate $\theta_3$ of the microregion $A1_3$ is $2\alpha$ and the value of the polar coordinate $\theta_4$ of the microregion $A1_4$ is $3\alpha$.

Figure 19B:
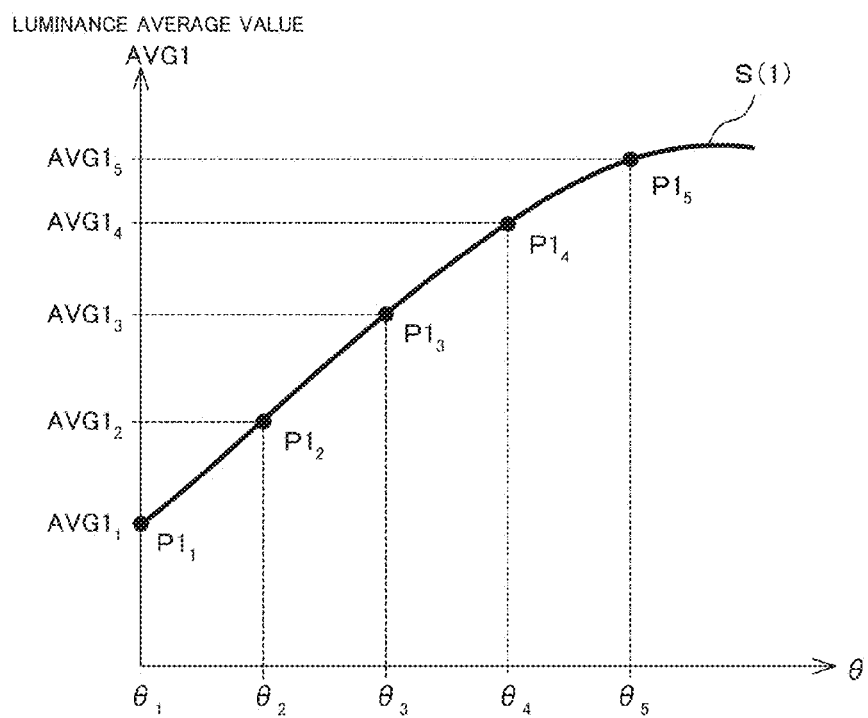
FIG. 19B is a drawing for explaining the method of generating the characteristic curve S(1).

The characteristic curve generating unit 37 next plots on the above-described coordinates a point $P1_1$ determined by the luminance average value $AVG1_1$ and the polar coordinate $\theta_1$ of the microregion $A1_1$, a point $P1_2$ determined by the luminance average value $AVG1_2$ and the polar coordinate $\theta_2$ of the microregion $A1_2$, and a point $P1_3$ determined by the luminance average value $AVG1_3$ and the polar coordinate $\theta_3$ of the microregion $A1_3$, and so forth for the 256 points $P1_i$ determined by the luminance average values $AVG1_i$ and the polar coordinates $\theta_i$ of the microregions $A1_i$, as can be seen by referring to FIG. 19B. Next, the characteristic curve generating unit 37 generates a curve passing through the 256 points $P1_i$ and makes this curve the characteristic curve S(1).

Next, the characteristic curve generating unit 37 computes the characteristic curve S(2) showing the relationship between the polar coordinates of the microregions $A2_i$ and the luminance average value computed for each of the microregions $A2_i$. Next, the characteristic curve generating unit 37 computes the characteristic curve S(3) showing the relationship between the polar coordinates of the microregions $A3_i$ and the luminance average value computed for each of the microregions $A3_i$. Next, the characteristic curve generating unit 37 computes the characteristic curve S(4) showing the relationship between the polar coordinates of the microregions $A4_i$ and the luminance average value computed for each of the microregions $A4_i$. Next, the characteristic curve generating unit 37 computes the characteristic curve S(5) showing the relationship between the polar coordinates of the microregions $A5_i$ and the luminance average value computed for each of the microregions $A5_i$. Next, the characteristic curve generating unit 37 computes the characteristic curve S(6) showing the relationship between the polar coordinates of the microregions $A6_i$ and the luminance average value computed for each of the microregions $A6_i$. Next, the characteristic curve generating unit 37 computes the characteristic curve S(7) showing the relationship between the polar coordinates of the microregions $A7_i$ and the luminance average value computed for each of the microregions $A7_i$. Next, the characteristic curve generating unit 37 computes the characteristic curve S(8) showing the relationship between the polar coordinates of the microregions $A8_i$ and the luminance average value computed for each of the microregions $A8_i$. Furthermore, the characteristic curve generating unit 37 outputs information relating to the characteristic curves S(1) to S(8) to the code generating unit 38.

The code generating unit 38 computes each of the slopes $M1(i)$ at $\theta_i$ of the characteristic curve S(1) showing the change in the luminance of the annular region A1. Furthermore, the code generating unit 38 generates a code 1 [M1(1), M1(2), . . . , M1(256)] by arranging the polarity of these slops in the order of polar coordinates $\theta_i$. For example, when the polarities of the slopes at $\theta_i$ of the characteristic curve S(1) are one of the three values +, – and 0, as shown in FIG. 20A, the code 1 [M1(1), M1(2), . . . , M1(256)] becomes a code in which +, – and 0 are arranged, as shown in FIG. 20B.

Next, the code generating unit 38 similarly generates a code 2 [M2(1), M2(2), . . . , M2(256)], a code 3 [M3(1), M3(2), . . . , M3(256)], a code 4 [M4(1), M4(2), . . . , M4(256)], a code 5 [M5(1), M5(2), . . . , M5(256)], a code 6 [M6(1), M6(2), . . . , M6(256)], a code 7 [M7(1), M7(2), . . . , M7(256)] and a code 8 [M8(1), M8(2), . . . , M8(256)]. Furthermore, the code generating unit 38 outputs the above-described eight codes 1 to 8 as a single comparison target code set to the comparison unit 39.

The comparison unit 39 stores data relating to multiple code sets composed of eight codes related to specific individual information and generated on the basis of a specified iris image by a process similar to the process described above. The comparison unit 39 compares the above-described comparison target code set and code sets stored in advance (hereafter called comparison code sets). Furthermore, when a comparison code set is specified whose degree of similarity to the comparison target code set is at least as great as a prescribed value, the comparison unit 39 outputs that result and individual information linked to the comparison code set to the outside. On the other hand, when no comparison code set is specified whose degree of similarity to the comparison target code set is at least as great as a prescribed value, the comparison unit 39 outputs that result to the outside.

As described above, with this first embodiment, characteristic curves S(1) to S(8) corresponding to eight annular regions A1 to A8 formed by partitioning the image of an iris are generated, and by arranging the polarities of the slopes of these characteristic curves, comparison target codes 1 to 8 are respectively generated. Because these comparison target codes 1 to 8 are codes composed of combinations of the three values +, − and 0, it is possible to reduce the data volume handled during comparison, the result being that it is possible to compare the comparison target codes in a short time.

Specifically, the data volume compared is reduced in comparison to the case of directly comparing the waveforms of the characteristic curves S(1) to S(8) generated on the basis of the image from the image capturing device 10 and the waveforms of characteristic curves acquired in advance. As a result, it is possible to compare the comparison target codes in a short time.

In addition, with this first embodiment, 256 microregions were established by partitioning the annular regions A1 to A8, but this is not limiting, for quadrilateral regions formed by connecting the end points of one set of arcs in a corresponding relationship in adjacent circles may be established along each of the annular regions A1 to A8.

In addition, with this first embodiment, an explanation was given for the case in which 256 microregions were defined in each of the annular regions A1 to A8, but this is not limiting, for fewer than 256 microregions may be defined, for example, or more than 256 microregions may be defined.

(Second Embodiment)

Next, a second embodiment of the present invention will be described with reference to FIGS. 21 to 23. Constituent elements that are the same or equivalent to those of the above-described first embodiment use the same reference numbers and explanation of such is omitted or simplified.

The biometric authentication apparatus 2 according to this embodiment differs from the biometric authentication apparatus 1 according to the above-described first embodiment in that the comparison apparatus 30 is realized through a composition similar to an apparatus such as a typical computer or workstation.

Figure 21:
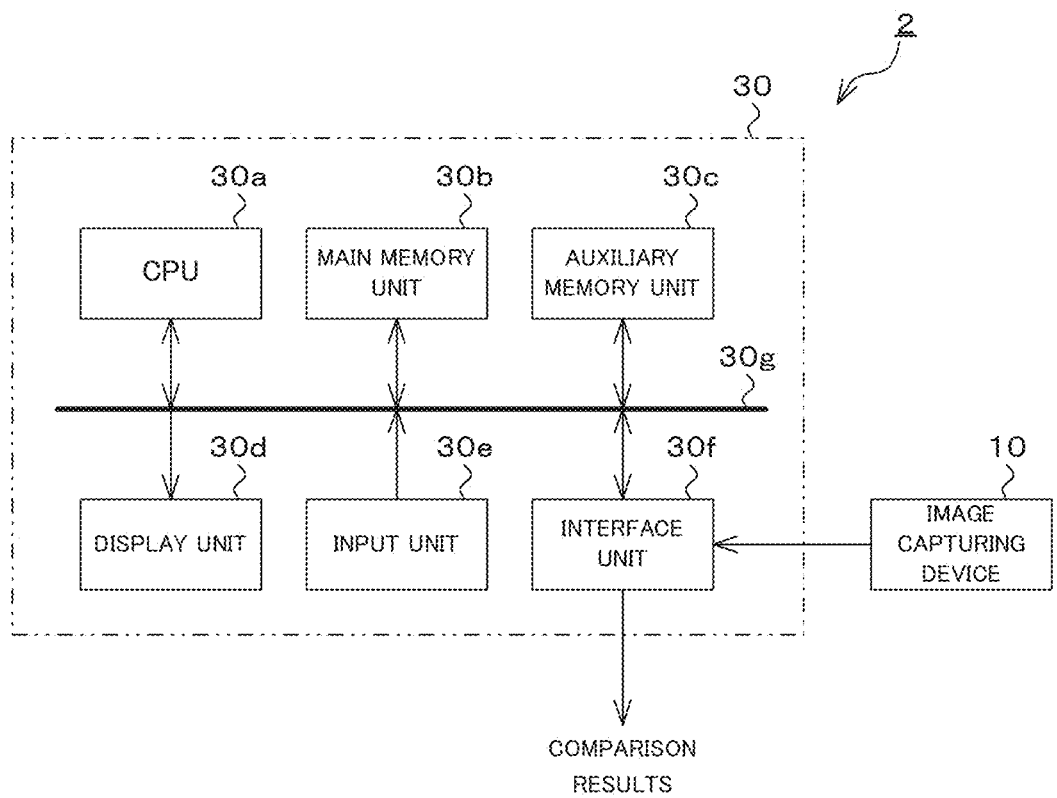
FIG. 21 is a block diagram of a biometric authentication apparatus according to a second embodiment of the present invention.

FIG. 21 is a block diagram showing the physical composition of the biometric authentication apparatus 2. As shown in FIG. 21, the biometrical authentication apparatus 2 is provided with an image capturing device 10 and a comparison apparatus 30 composed of a computer.

The comparison apparatus 30 has a CPU (Central Processing Unit) 30a, a main memory unit 30b, an auxiliary memory unit 30c, a display unit 30d, an input unit 30e, an interface unit 30f and a system bus 30g that connects all of the above-described units to each other.

The CPU 30a executes the below-described image processing on an image P captured by the image capturing device 10 following a program stored in the auxiliary memory unit 30c.

The main memory unit 30c has RAM (Random Access Memory) or the like. The main memory unit 30b is used as a work region for the CPU 30a.

The auxiliary memory unit 30c has non-volatile memory such as ROM (Read Only Memory), a magnetic disc, semiconductor memory or the like. This auxiliary memory unit 30c stores a program executed by the CPU 30a and various types of parameters. In addition, the auxiliary memory unit 30c stores information including the processing results of the CPU 30a.

The display unit 30d has a CRT (Cathode Ray Tube) or an LCD (Liquid Crystal Display). The display unit 30d displays the processing results of the CPU 30a. In this embodiment, each time a process is executed on the digital image P, a binary image P2, an image P3 or the like is displayed on the display unit 30d as those process results.

The input unit 30e has a keyboard and a pointing device such as a mouse. Instructions from the operator are input via this input unit 30e and are conveyed to the CPU 30a via the system bus 30g.

The interface unit 30f has a serial interface or a LAN (Local Area Network) interface. The image capturing device 10 is connected to the system bus 30g via the interface unit 30f.

Figure 22:
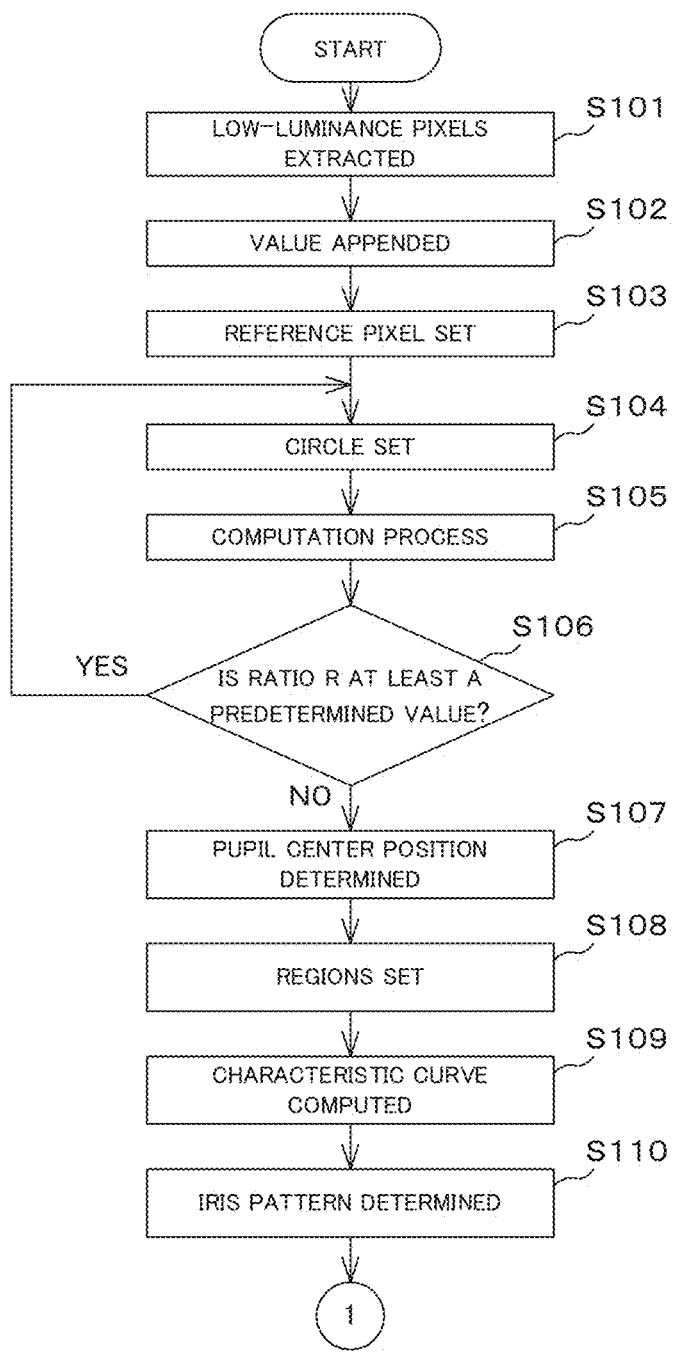
FIG. 22 is a flowchart (part 1) showing the operation of a comparison apparatus.
Figure 23:
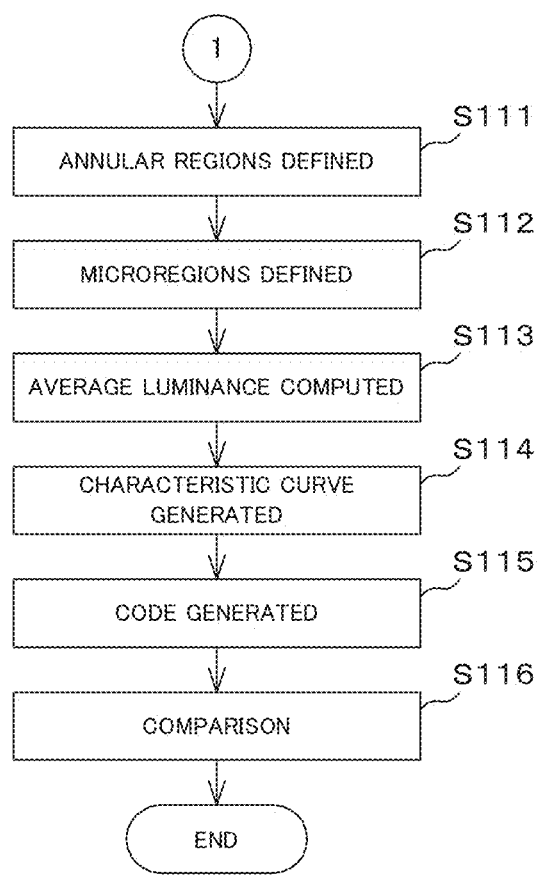
FIG. 23 is a flowchart (part 2) showing the operation of a comparison apparatus.

The flowcharts in FIG. 22 and FIG. 23 correspond to a series of process algorithms of a program executed by the CPU 30a of the comparison apparatus 30. Image processing in the comparison apparatus 30 is described below with reference to FIGS. 22 and 23. This image processing is realized by the CPU 30a comprehensively controlling the main memory unit 30b, the auxiliary memory unit 30c, the display unit 30d and the interface unit 30f in accordance with a program read from the auxiliary memory unit 30c.

First, the CPU 30a extracts low-luminance pixels whose luminance is less than a prescribed value from among the multiple pixels comprising the digital image P captured by the image capturing device 10 (step S101). More specifically, the CPU 30a extracts low-luminance pixels from the binary image P2 obtained through image conversion of the digital image P using a prescribed threshold value.

Next, the CPU 30a successively selects extracted low-luminance pixels, and appends the value 1, for example, to each of the multiple pixels within a prescribed distance from each selected low-luminance pixel (step S102).

Next, the CPU 30a sets the pixel with the highest sum of appended values as the reference pixel $PX_0$ (step S103). The position of the reference pixel $PX_0$ substantially matches the center of the pupil of the eye shown in the image P1 (see FIG. 9).

Next, the CPU 30a sets a circle C(1) centered at the reference pixel $PX_0$ and a circle C(2) having a radius larger than the radius of the circle C(1) (step S104).

Next, the CPU 30a accomplishes computation processes (step S105). Here, the CPU 30a first computes the areas $S_1$ and $S_2$ of the circles C(1) and C(2), respectively, and the number $N_1$ and $N_2$ of low-luminance pixels inside the circles C(1) and C(2), respectively. Next, the CPU 30a computes the ratio $R_N$ of the number of low-luminance pixels $(N_2-N_1)$ in each of the circles to the difference in surface areas $(S_2-S_1)$ of the circles C(1) and C(2) (here, $R_1 (=(N_2-N_1/(S_2-S_1)))$.

Next, the CPU 30a determines whether or not this ratio $R_N$ is at least as large as a prescribed value (step S106). Furthermore, when this ratio $R_N$ is at least as large as the prescribed value (step S106; Yes), the CPU 30a returns to step S104.

In this case, the CPU 30a sets a circle C(3) having a radius larger than the radius of the circle C(2) (step S104). Furthermore, the CPU 30a computes the ratio $R_2 (=(N_3-N_2)/(S_3-S_2))$ of the number of low-luminance pixels $(N_3-N_2)$ in each of the circles to the difference in surface areas $(S_3-S_1)$ of the circles C(2) and C(3) (step S105). Following this, the process from step S104 to step S106 is repeated until the ratio $R_N$ falls below the prescribed value (step 106; No).

When the ratio $R_N$ falls below the prescribed value (step S106; No), the CPU 30a moves to step S107. For example, as shown in FIG. 11, when the circle C(4) protruding from the region defined by the pixel groups PG1 and PG2 is set, the determination in step S106 is negative.

Next, the CPU 30a searches for the center position $P_t$ of the circle C(4) when the number of low-luminance pixels contained in the circle C(4) becomes a maximum while moving the circle C(4) with the reference pixel $PX_0$ as the reference position, and designates the position $P_1$ found as the center of the pupil (step S107).

Next, the CPU 30a establishes multiple arc-shaped microregions (step S108). Here, the CPU 30a first defines an x-y coordinate system on the image P1 with the position $P_1$ as the origin, and defines triangular region F1 and region F2 defined by the straight lines L1 and L2 forming an angle of 15 degrees with the x-axis with the position $P_i$ as the starting point on the image P1. Next, the CPU 30a establishes multiple arc-shaped microregions by partitioning the region F1 by multiple arcs whose central angles are angles defined by the x-axis and the straight line L1 (see FIG. 14A). Furthermore, the CPU 30a establishes multiple arc-shaped microregions by partitioning the region F2 by multiple arcs whose central angles are angles defined by the x-axis and the straight line L2.

Next, the CPU 30a computes the average value of the luminance of pixels contained in the microregions for each of the microregions belonging to the region F1 or the region F2, and computes a characteristic curve SL expressing the relationship between the position of the microregion on the x-axis and the corresponding average value of the luminance (step S109).

Next, the CPU 30a designates an iris pattern (step S110). More specifically, the CPU 30a finds the x-coordinates A and D at the intersection of the x-axis and the iris outer edge on the basis of the degree of change in this characteristic curve SL, and designates that the image of the iris is positioned in the region defined by the circle C(4) on the image P1 and the circle Cq(0) (see FIG. 15).

Next, as shown in FIG. 23, the CPU 30a defines annular regions by partitioning the region defined by the circle C(4) substantially matching the outer edge of the pupil and the circle Cq(0) substantially matching the outer edge of the iris into eight annular regions (see FIG. 16) using the seven circles Cq(1) to Cq(7) (step S111).

Next, the CPU 30a defines microregions by partitioning the eight annular regions A1 to A8 into 256 microregions each (step S112). More specifically, the CPU 30a partitions the circles C(4) and Cq(7) into arcs whose center angle is a (360/256), with the intersection between the respective circles and the x-axis as reference points, and partitions the annular region A1 into 256 microregions $A1_1$ to $A1_{256}$ by defining a line linking the end points of the arcs with a corresponding relationship. Similarly, the CPU 30a (microregion specifying unit 35) partitions the annular regions A2 to A8 into microregions $A2_1$ to $A2_{256}$, microregions $A3_1$ to $A3_{256}$, microregions $A4_1$ to $A4_{256}$, microregions $A5_1$ to $A5_{256}$, microregions $A6_1$ to $A6_{256}$, microregions $A7_1$ to $A7_{256}$ and microregions $A8_1$ to $A8_{256}$, respectively.

Next, the CPU 30a first finds the average value (average luminance) $AVG1_i$ of the luminance of the pixels contained the microregion $A1_i$ (I=1, 2, ..., 256) for each of the microregions $A1_1$ to $A1_{256}$ belonging to the annular region A1 (step S113). Next, the CPU 30a (microregion specifying unit 35) finds the average values $AVG2_i$ to $AVG8_i$ of the luminance of the pixels respectively contained in the microregions $A2_i$ to $A8_i$ belonging to the annular regions A2 to A8.

Next, the CPU 30a computes characteristic curves S(1) to S(8) indicating the relationship between the polar coordinates of the microregions $A1_i$ to $A8_i$ and the average value of the luminance computed for each of the microregions $A1_i$ to $A8_i$ (step S114).

Next, the CPU 30a generates codes (step S115). Here, the CPU 30a (code generating unit 38) first computes the slope M1(i) at $\theta_i$ of the characteristic curve S(1) showing the change in the luminance of the annular region A1. Furthermore, the CPU 30a (code generating unit 38) generates a code 1 [M1(1), M1(2), ..., M1(256)] by arranging the polarities of these slops in order of polar coordinates $\theta_i$. Similarly, the CPU 30a (code generating unit 38) generates a code 2 [M2(1), M2(2), ..., M2(256)], a code 3 [M3(1), M3(2), ..., M3(256)], a code 4 [M4(1), M4(2), ..., M4(256)], a code 5 [M5(1), M5(2), ..., M5(256)], a code 6 [M6(1), M6(2), ..., M6(256)], a code 7 [M7(1), M7(2), ..., M7(256)] and a code 8 [M8(1), M8(2), ..., M8(256)].

Next, the CPU 30a compares the above-described comparison target code set with code sets (hereafter called comparison code sets) stored in advance (step S116). Furthermore, when a comparison code set is specified whose degree of similarity to the comparison target code set is at least as great as a prescribed value, the CPU 30a outputs that result and individual information linked to the comparison code set to the outside. On the other hand, when no comparison code set is specified whose degree of similarity to the comparison target code set is at least as great as a prescribed value, the CPU 30a outputs that result to the outside.

As described above, with this second embodiment, characteristic curves S(1) to S(8) corresponding to eight annular regions A1 to A8 formed by partitioning the image of an iris are generated, and by arranging the polarities of the slopes of these characteristic curves, comparison target codes 1 to 8 are respectively generated. Because these comparison target codes 1 to 8 are codes composed of combinations of the three values +, − and 0, it is possible to reduce the data volume handled during comparison, the result being that it is possible to compare the comparison target codes in a short time.

Specifically, the data volume compared is reduced in comparison to the case of directly comparing the waveforms of the characteristic curves S(1) to S(8) generated on the basis of the image from the image capturing device 10 and the waveforms of characteristic curves acquired in advance. As a result, it is possible to compare the comparison target codes in a short time.

(Third Embodiment)

Next, a third embodiment of the present invention will be described with reference to FIGS. 24 to 26. Constituent elements that are the same or equivalent to those of the above-described first embodiment and the above-described second embodiment use the same reference numbers and explanation of such is omitted or simplified.

Figure 24:
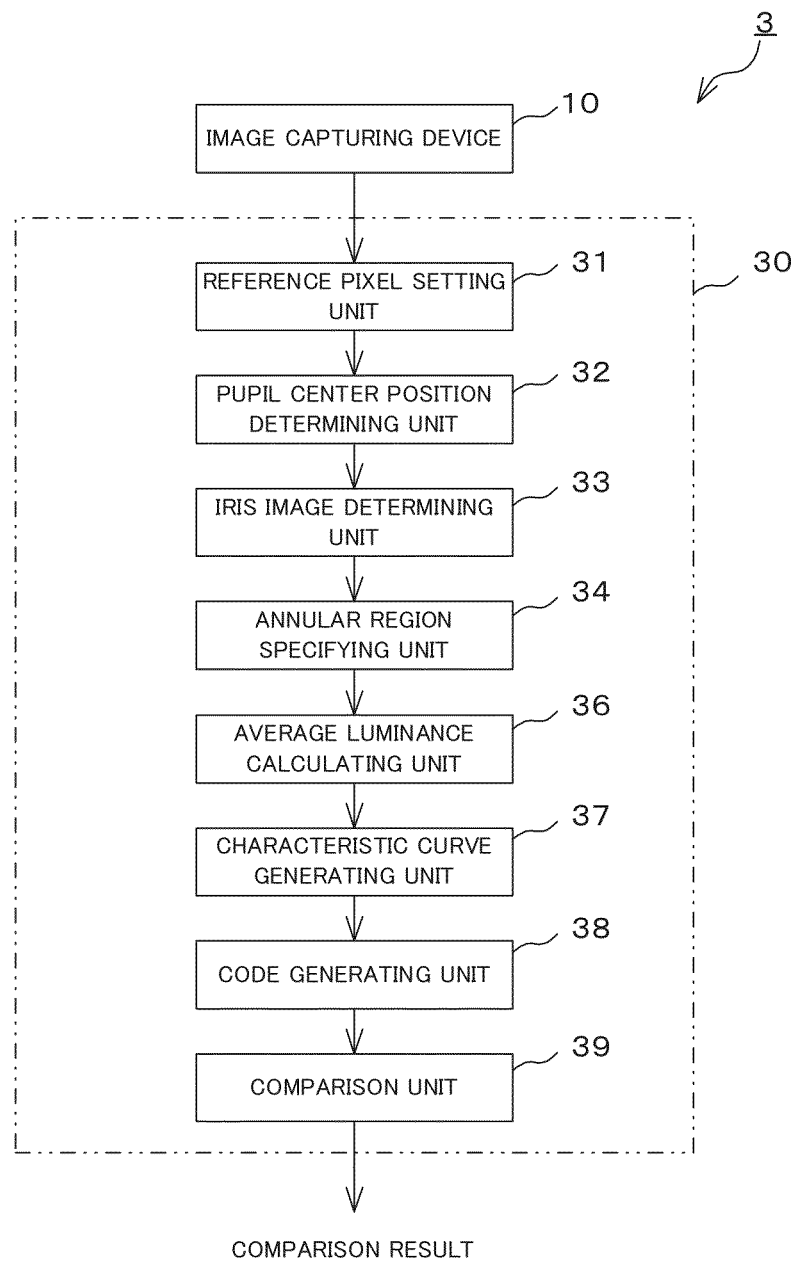
FIG. 24 is a block diagram of a biometric authentication apparatus according to a third embodiment of the present invention.
Figure 25:
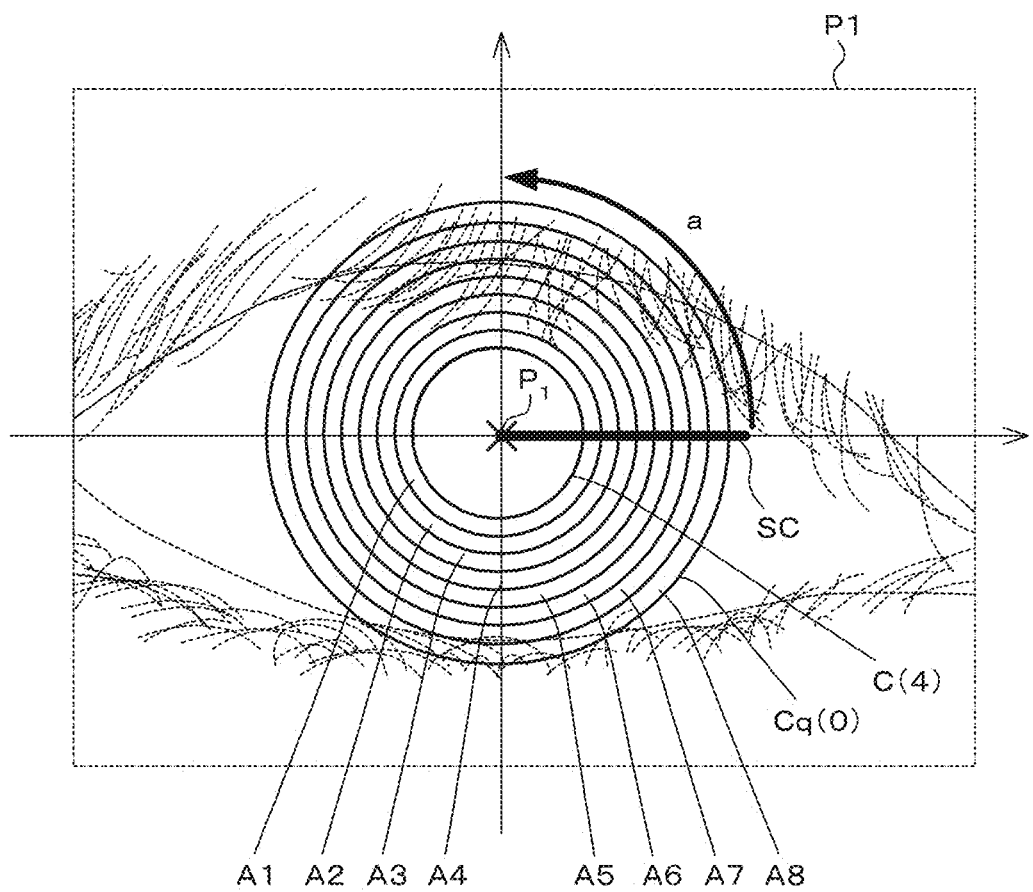
FIG. 25 is a drawing used to explain the operation of an average luminance computation unit

FIG. 24 is a block diagram of a biometric authentication apparatus 3 according to this embodiment. As shown in FIG. 24, the biometric authentication apparatus 3 differs from the biometric authentication apparatus 1 according to the above-described first embodiment in not having a microregion specifying unit 35 for defining microregions by partitioning the annular regions A1 to A8 and in that the average luminance calculating unit 36 comprising the comparison apparatus 30 performs a different action.

The operation of the average luminance calculating unit 36 according to this embodiment is described below. As one example, in FIG. 25 an image P1 defined by the annular regions A1 to A8 and a line segment SC that rotates about the center point $P_1$ of the circle C(4) are shown. The average luminance calculating unit 36 defines the line segment SC having one edge on the center point $P_1$ and the other end on the outside of the circle Cq(0), as shown in FIG. 25.

Next, the average luminance calculating unit 36 causes this line segment Sc to rotate in the direction indicated by an arrow a about the center point $P_1$ and at the same time computes the average luminance of pixels overlapping the line segment Sc out of the pixels contained in the annular regions A1 to A8, respectively, for each of the annular regions A1 to A8. Furthermore, the average luminance calculating unit 36 outputs to the characteristic curve generating unit 37 the computed average luminances $AVG1_{\theta rot}$ to $AVG\ 8_{\theta rot}$, linked to the angle of rotation of the line segment.

The characteristic curve generating unit 37 generates eight characteristic curves g(1) to g(8) corresponding to the annular regions A1 to A8, respectively, by plotting points determined by the angle of rotation $\theta_{rot}$ of the line segment and the average luminances $AVG1_{\theta rot}$ to $AVG\ 8_{\theta rot}$ for each of the annular regions A1 to A8, on coordinates having the angle on the horizontal axis and the average luminance on the vertical axis.

Figure 26:
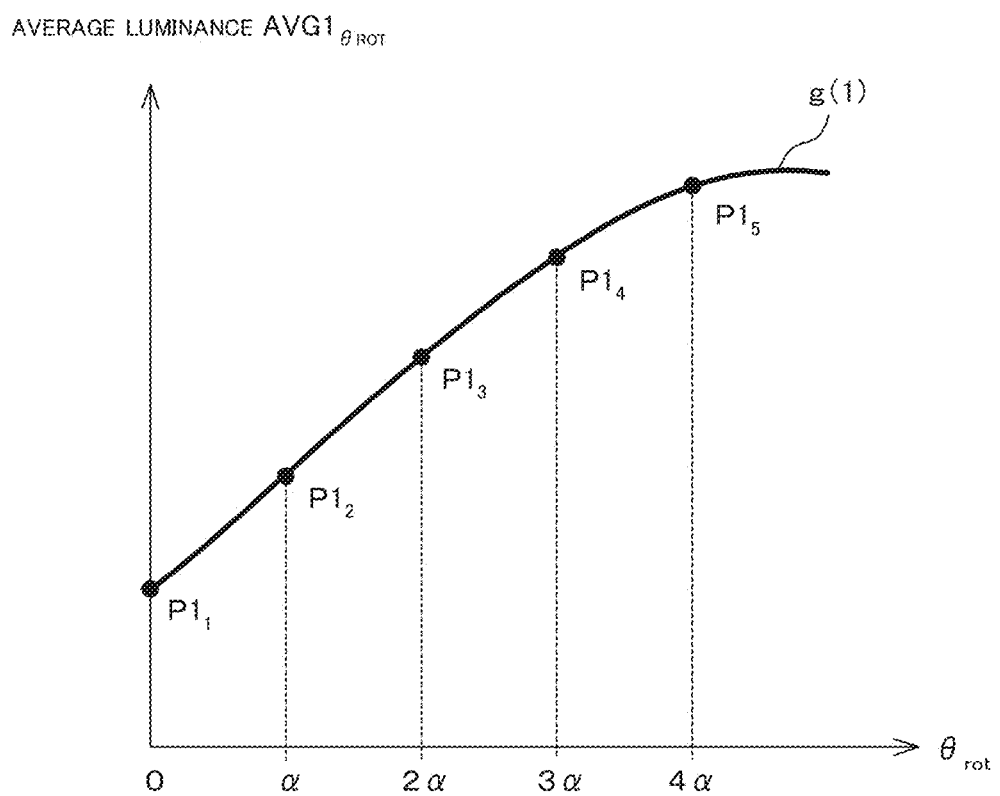
FIG. 26 is a drawing for explaining the method of generating a characteristic curve g(1).

When the characteristic curves g(1) to g(8) are generated, the code generating unit 38 first computes for the characteristic curve g(1) the slopes M1(j·α) of the characteristic curve g(1) for each angle α (360/256) with 0 as the starting point, as can be seen by referring to FIG. 26.

Furthermore, the code generating unit 38 generates a code 1 [M1(0), M1(α), M1(2·α), . . . , M1(255·α)] that is a combination of the three values +, − and 0 by arranging in order of $\theta_{rot}$ the polarities of those slopes M1(j·α). Similarly, the code generating unit 38 generates a code 2 [M2(0), M2(α), M2(2·α), . . . , M2(255·α)], a code 3 [M3(0), M3(α), M3(2·α), . . . , M3(255·α)], a code 4 [M4(0), M4(α), M4(2·α), . . . , M4(255·α)], a code 5 [M5(0), M5(α), M5(2·α), . . . , M5(255·α)], a code 6 [M6(0), M6(α), M6(2·α), . . . , M6(255·α)], a code 7 [M7(0), M7(α), M7(2·α), . . . , M7(255·α)] and a code 8 [M8(0), M8(α), M8(2·α), . . . , M8(255·α)] corresponding to the characteristic curves g(2) to g(8). Furthermore, the code generating unit 38 outputs the above-described eight codes 1 to 8 to the comparison unit 39 as a comparison target code set.

The comparison unit 39 compares the above-described comparison target code set to code sets stored in advance (hereafter called comparison code sets). Furthermore, when a comparison code set is specified whose degree of similarity to the comparison target code set is at least as great as a prescribed value, the comparison unit 39 outputs that result and individual information linked to the comparison code set to the outside. On the other hand, when no comparison code set is specified whose degree of similarity to the comparison target code set is at least as great as a prescribed value, the comparison unit 39 outputs that result to the outside.

As described above, with this third embodiment characteristic curves g(1) to g(8) are generated by each of the eight annular regions A1 to A8 being scanned using the line segment SC. Furthermore, comparison target codes 1 to 8 are respectively generated by arranging the polarities of the slopes of these characteristic curves g(1) to g(8) in order of the rotation angle of the line segment SC. Because these comparison target codes 1 to 8 are codes composed of combinations of the three values +, − and 0, it is possible to reduce the data volume handled during comparison, the result being that it is possible to compare the comparison target codes in a short time.

With this third embodiment, curves obtained by plotting points determined by the angle of rotation $\theta_{rot}$ of the line segment SC and the average luminances $AVG1_{\theta rot}$ to $AVG8_{\theta rot}$ are generated as the eight characteristic curves g(1) to g(8) corresponding to the annular regions A1 to A8, respectively. However, the present invention is not limited to this, for the characteristic curves g(1) to g(8) may also be curves resulting from a smoothing process being accomplished on curves obtained by plotting points determined by the angle of rotation $\theta_{rot}$ of the line segment and the average luminances $AVG1_{\theta rot}$ to $AVG8_{\theta rot}$. As this smoothing process, it is possible to utilize a process for smoothing the curves using the moving average method, for example.

In addition, in this third embodiment a scan of the annular regions A1 to A8 was accomplished by causing the line segment SC to rotate about a center point $P_1$, but this is not intended to be limiting, for a scan may also be accomplished by causing the line segment SC to rotate about a reference pixel $PX_0$, for example, and in addition a scan may be accomplished by causing the line segment SC to rotate about the center point $Q_0$ of the circle Cq(0) defining the outer edge of the image of the iris.

Various embodiments of the present invention were described above, but these are intended to be illustrative and not limiting.

In addition, the functions of the comparison apparatus 30 according to the above-described embodiments can be realized through specialized hardware or through a normal computer system.

The programs stored in the auxiliary memory unit 30c of the comparison apparatus 30 in the second embodiment may be by stored and distributed on a computer-readable recording medium such as a flexible disk, a CD-ROM (Compact Disk Read-Only Memory), a DVD (Digital Versatile Disk), a MO (Magneto-Optical disk) or the like, and the apparatus for executing the above-described process may be composed by installing those programs on a computer.

In addition, the above-described programs may be stored on a disk apparatus or the like of a prescribed server on a communication network such as the Internet, and for example, may be downloaded to a computer by being overlaid on carrier waves.

In addition, the above-described programs may be launched and executed while being transmitted via a communication network.

In addition, the above-described programs may be executed in whole or in part on a server, and the above-described image processing may be executed while sending and receiving information relating to that process via a communication network.

When the above-described functions are realized by allocation to the OS (Operating System) or are realized through cooperation between the OS and applications, parts other than the OS may be stored and distributed on a medium, and in addition, may be downloaded to a computer.

Having described and illustrated the principles of this application by reference to one or more preferred embodiments, it should be apparent that the preferred embodiment(s) may be modified in arrangement and detail without departing from the principles disclosed herein and that it is intended that the application be construed as including all such modifications and variations insofar as they come within the spirit and scope of the subject matter disclosed herein.

INDUSTRIAL APPLICABILITY

The biometric authentication apparatus, biometric authentication method and recording medium according to the present invention are suitable for accomplishing authentication using the iris pattern of an eye.

EXPLANATION OF SYMBOLS 1-3 biometric authentication apparatus
10 image capturing device
30 comparison apparatus
30a CPU
30b main memory unit 30c auxiliary memory unit
30d display unit
30e input unit
30f interface unit
30g system bus
31 reference pixel setting unit
32 pupil center position determining unit
33 iris image determining unit
34 annular region specifying unit
35 microregion specifying unit
36 average luminance calculating unit
37 characteristic curve generating unit
38 code generating unit
39 comparison unit
P digital image
P1 image
P2 binary image
P3 image
PX pixel
PX0 reference pixel
PG1 low-luminance pixel group
PG2 high-luminance pixel group
F1, F2 regions
A1-A8 annular regions
C, Cq circles

The invention claimed is:

1. A biometric authentication apparatus, comprising: a curve calculating unit which is implemented in a processor and which is configured for calculating, based on a digital image of an iris, curves showing a relationship between polar coordinates indicating a position of the iris on the digital image and luminance of pixels of the digital image of the iris corresponding to coordinate values of the polar coordinates; and a code generating unit which is implemented in a processor and which is configured for generating a comparison target code by arranging three values based on polarities of slopes of the curves in order of the polar coordinates, wherein the three values include +, −, and 0.

2. The biometric authentication apparatus according to claim 1, wherein the curve calculating unit possesses:
   a first partitioning unit which is implemented in a processor and which is configured for partitioning the digital image of the iris into multiple annular regions;
   a second partitioning unit which is implemented in a processor and which is configured for partitioning each of the annular regions into multiple microregions corresponding to a polar coordinate having an origin that is a center of a circle defining the inside edge of the annular region;
   a computing unit which is implemented in a processor and which is configured for calculating the average value of the luminance of the pixels contained in the microregions for each annular region; and
   a generating unit which is implemented in a processor and which is configured for generating, for each of the annular regions, a curve showing the relationship between the polar coordinate having the origin that is the center of the circle defining the inside edge for the annular region and the average value of the luminance in the microregions for the annular region.

3. The biometric authentication apparatus according to claim 1, wherein the polarities of the slopes of the curve are each one of the three values consists of a positive value, a negative value, and zero.

4. A biometric authentication method, comprising: a process for calculating, based on a digital image of an iris, curves showing a relationship between polar coordinates indicating a position of the iris on the digital image and luminances of pixels comprising of digital image of the iris corresponding to coordinate values of the polar coordinates; and a process for generating a comparison target code by arranging three values based on polarities of slopes of the curves in order of the polar coordinates, wherein the three values include +, −, and 0.

5. A non-transitory computer-readable recording medium on which is recorded a program that causes a computer to function as:
   a means for calculating, based on a digital image of an iris, curves showing a relationship between polar coordinates indicating a position of the iris on the digital image and luminances of pixels of the digital image of the iris corresponding to coordinate values of the polar coordinates; and
   a means for generating a comparison target code by arranging three values based on polarities of slopes of the curves in order of the polar coordinates, wherein the three values include +, −, and 0.

* * * * *